United States Patent
Tsoi et al.

(10) Patent No.: US 11,464,443 B2
(45) Date of Patent: Oct. 11, 2022

(54) METHODS BASED ON AN ANALYSIS OF DRAWING BEHAVIOR CHANGES FOR COGNITIVE DYSFUNCTION SCREENING

(71) Applicant: The Chinese University of Hong Kong, Hong Kong (CN)

(72) Inventors: Kam Fai Tsoi, Hong Kong (CN); Wing Yip Lam, Hong Kong (CN); Tsz Kan Christopher Chu, Hong Kong (CN); Ka Ho Tsang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 236 days.

(21) Appl. No.: 16/696,270

(22) Filed: Nov. 26, 2019

(65) Prior Publication Data
US 2021/0153801 A1 May 27, 2021

(51) Int. Cl.
G06K 9/00 (2022.01)
A61B 5/00 (2006.01)
G16H 10/20 (2018.01)
G06K 9/62 (2022.01)
(Continued)

(52) U.S. Cl.
CPC ............ *A61B 5/4088* (2013.01); *G06F 17/16* (2013.01); *G06K 9/6218* (2013.01); *G06K 9/6259* (2013.01); *G06K 9/6278* (2013.01); *G06K 9/6296* (2013.01); *G06V 10/751* (2022.01); *G16H 10/20* (2018.01)

(58) Field of Classification Search
CPC ...... A61B 5/4088; G16H 10/20; G06F 17/16; G06K 9/6202; G06K 9/6218; G06K 9/6259; G06K 9/6278; G06K 9/6296
See application file for complete search history.

(56) References Cited

U.S. PATENT DOCUMENTS

| 10,383,553 B1 * | 8/2019 | Glenn ...................... A61B 5/16 |
| 2007/0123757 A1 * | 5/2007 | Chervinsky .............. A61B 5/16 600/300 |

(Continued)

OTHER PUBLICATIONS

Tsoi, Kelvin KF, et al. "Machine Learning on Drawing Behavior for Dementia Screening." Proceedings of the 2018 International Conference on Digital Health. 2018. (Year: 2018).*

(Continued)

*Primary Examiner* — Avinash Yentrapati
(74) *Attorney, Agent, or Firm* — Saliwanchik, Lloyd & Eisenschenk

(57) ABSTRACT

Methods for screening, diagnosing, or predicting presence, progression, or treatment effects of a cognitive dysfunction such as dementia based on an analysis of drawing behavior changes by a pre-trained Naïve Bayes method are provided. The methods include steps of obtaining drawing data of at least one image created by a test subject on a digital device and obtaining personal data of the test subject; reconstructing the at least one image based on the drawing data obtained; converting the drawing data to drawing features comprising a plurality of motion features and a plurality of geometric features; and determining probability that the test subject has a cognitive dysfunction based on the drawing features and the personal data by a pre-trained Naïve Bayes method with a greedy variable selection.

20 Claims, 19 Drawing Sheets

(51) Int. Cl.
G06F 17/16 (2006.01)
G06V 10/75 (2022.01)

(56) References Cited

U.S. PATENT DOCUMENTS

| | | | | |
|---|---|---|---|---|
| 2008/0118899 | A1* | 5/2008 | Sahakian | A61B 5/4088 434/236 |
| 2013/0216986 | A1* | 8/2013 | Goldman | G09B 19/00 434/236 |
| 2014/0031724 | A1* | 1/2014 | Davis | A61B 5/165 600/595 |
| 2016/0154010 | A1* | 6/2016 | O'Bryant | G16B 20/00 600/300 |
| 2016/0262680 | A1* | 9/2016 | Martucci | G09B 7/00 |
| 2018/0133431 | A1* | 5/2018 | Malchano | A61N 1/36132 |
| 2019/0076078 | A1* | 3/2019 | Davis | A61B 5/1101 |

OTHER PUBLICATIONS

Lin, J. S. et al., "Screening for Cognitive Impairment in Older Adults: A Systematic Review for the U.S. Preventative Services Task Force," *Annals of Internal Medicine*, Nov. 5, 2013, 159(9):601-612.

Plassman, B.L. et al., "Prevalence of Dementia in the United States: The Aging, Demographics, and Memory Study," *Neuroepidemiology*, 2007, 29:125-132, S. Karger AG.

Valcour, V. G. et al., "The Detection of Dementia in the Primary Care Setting," *Arch Intern Med*, Oct. 23, 2000, 160:2964-2968, American Medical Association.

Chodosh, J. et al., "Physician Recognition of Cognitive Impairment: Evaluating the Need for Improvement," *Journal of the American Geriatrics Society*, Jul. 2004, 52(7):1051-1059, American Geriatrics Society.

Llife, S. et al., "Sooner or later? Issues in the early diagnosis of dementia in general practice: a qualitative study," *Family Practice*, 2003, 20(4):376-381, Oxford University Press.

Mitchell, A. J., "The clinical significance of subjective memory complaints in the diagnosis of mild cognitive impairment and dementia: a meta-analysis," *International Journal of Geriatric Psychiatry*, 2008, 23:1191-1202, John Wiley & Sons, Ltd.

Mitchell, A. J. et al., "Risk of dementia and mild cognitive impairment in older people with subjective memory complaints: meta-analysis," *Acta Psychiatrica Scandinavica*, 2014, 130:439-451. John Wiley & Sons.

Ashford, J. W. et al., "Should older adults be screened for dementia?" *Alzheimer's & Dementia*, 2006, 2:76-85, The Alzheimer's Association.

Souillard-Mandar, W. et al., "Learning Classification Models of Cognitive Conditions from Subtle Behaviors in the Digital Clock Drawing Test," *Mach Learn.*, Mar. 2016, 102(3):393-441.

Oxbury, J. M. et al., "Unilateral Spatial Neglect and Impairments of Spatial Analysis and Visual Perception," *Brain*, 1974, 97:551-564.

Lee, B. H. et al., "Mechanism of the Closing-in Phenomenon in a Figure Copying Task in Alzheimer's Disease Patients," *Neurocase*, 2004, 10(5):393-397, Taylor & Francis Inc.

Dansilio, S. et al., "Constructional functions and figure copying in illiterates or low-schooled Hispanics," *Archives of Clinical Neuropsychology*, 2005, 20:1105-1112, National Academy of Neuropsychology.

Watanabe, K. et al., "The Rey-Osterrieth Complex Figure as a measure of executive function in childhood," *Brain & Development*, 2005, 27:564-569, Elsevier B.V.

Shin, M. et al., "Clinical and empirical applications of the Rey-Osterrieth Complex Figure Test," *Nature Protocols*, 2006, 1(2):892-899.

Tchalenko, J. et al., "Eye-hand strategies in copying complex lines," *Cortex*, 2009, 45:368-376, 2008 Elsevier Srl.

Maeshima, S. et al., "Usefulness of a cube-copying test in outpatients with dementia," *Brain Injury*, Sep. 2004, 18(9):889-898, Taylor & Francis Ltd.

Buchhave, P. et al., "Cube Copying Test in Combination with rCBF or CSF $A\beta_{42}$ Predicts Development of Alzheimer's Disease," *Dementia and Geriatric Cognitive Disorders*, 2008, 25:544-552, S. Karger AG.

Bourke, J. et al., "Short Report a Comparison of Clock and Pentagon Drawing in Alzheimer'S Disease," *International Journal of Geriatric Psychiatry*, 1995, 10:703-705, John Wiley & Sons, Ltd.

Ala, T. A. et al., "Pentagon copying is more impaired in dementia with Lewy bodies than in Alzheimer's disease," *J. Neurol Neurosurg Psychiatry*, 2001, 70:483-488.

Cormack, F. et al., "Pentagon drawing and neuropsychological performance in Dementia with Lewy Bodies, Alzheimer's disease, Parkinson's disease, and Parkinson's disease with dementia," *International Journal of Geriatric Psychiatry*, 2004, 19:371-377, John Wiley & Sons, Ltd.

Caffarra, P. et al., "The qualitative scoring MMSE pentagon test (QSPT): A new method for differentiating dementia with Lewy Body from Alzheimer's disease," *Behavioural Neurology*, 2013, 27:213-220, IOS Press and the authors.

Mitolo, M. et al., "The New Qualitative Scoring MMSE Pentagon Test (QSPT) as a Valid Screening Tool between Autopsy-Confirmed Dementia with Lewy Bodies and Alzheimer's Disease," *J Alzheimers Dis.*, 2014, 39(4):823-832, IOS Press and the authors.

Alzheimer's Society United Against Dementia, "Factsheet 450LP," Apr. 2016, pp. 1-17, Alzheimer's Society, 2017.

Cagnin, A. et al., "High specificity of MMSE pentagon scoring for diagnosis of prodromal dementia with Lewy bodies," *Parkinsonism and Related Disorders*, 2015, 21:303-305, 2014 Elsevier Ltd.

* cited by examiner

METHODS BASED ON AN ANALYSIS OF DRAWING BEHAVIOR CHANGES FOR COGNITIVE DYSFUNCTION SCREENING

BACKGROUND OF THE INVENTION

Cognitive dysfunctions such as dementia may cause a loss of independent functions of an individual and have a wide-ranging impact on the individual, his/her family and the society. Clinical manifestations of Alzheimer's disease (AD), the most commonly known form of dementia, include a decline in cognitive function and impaired activities of daily living. Previous study has shown that the diagnosis of dementia is frequently missed in a proportion as much as 76%. Most dementia sufferers are not diagnosed until they are at a moderate-to-severe stage of the disease. Early detection of dementia is particularly important for enabling the patients to understand their symptoms and for allowing possible interventions at an earlier stage of the disease development.

Screening tests are quick and useful tools to assess the cognitive healthiness of the patients. Conventional clinical screening tests are mainly in paper-and-pencil forms and are conducted in face-to-face interviews which require screening participants to visit healthcare professionals in the clinics. Moreover, the screening procedures heavily rely on the guidance and the judgement of healthcare professionals. Due to the subjective nature of the evaluation, test subjects can be misdiagnosed.

Drawing Test (DT) has been employed to screen dementia of elderly. In a DT, participants are asked to copy a figure placed in front of them. One obvious advantage offered by all DTs is the wide applicability. DT does not require any language ability and knowledge base, as opposed to other types of screening tests. Numerous clinical studies have shown that poor performance in DT can reflect defects in different cognitive functions such as attention, spatial constructional ability, visual memory, executive functions, and processes associated with eye-hand coordination.

As dementia is characterized by decline in cognitive function, multiple cognitive domains including visuospatial skills, sustained attention, and executive function would be impaired accordingly. A simple figure copying task would require normal function in the aforementioned domains to complete. The test subjects have to be attentive to the sample figure and visualize the shape of the figure before using his/her hand to draw. Therefore, the test subjects with dementia require significantly more time to complete the task when comparing to the healthy test subjects. As test subjects are required to copy the given figure as similar as possible, demented test subjects tend to have longer thinking time and irregular drawing patterns, which could be indicated by the drawing process and the image drawn.

Digitized screening tests have been proved to be beneficial for their standardized format, minimized loss of information caused by the floor and ceiling effects, and precise record of human activities with a level of accuracy not achievable by the traditional tests. In recent 50 years, a digitized drawing task—Clock Drawing Test (CDT) has been used as a cognitive screening tool on test subjects with various forms of dementias including Alzheimer's disease, Parkinson's disease and other neurological disorders. During the test, the test subjects are required to draw a clock showing 10 minutes after 11 (called the Command clock) on a blank sheet of paper, and then asked to copy a pre-drawn clock showing that time (the Copy clock). A digital ballpoint pen is used to capture positions of the test subject's pen stroke data. Next, several prediction models are created based on machine learning algorithms. According to the results of the predictions, the best trained machine learning model without concerns of interpretability can achieve a F1 score as good as 0.86 for the screening tasks.

However, the CDT requires a designated device such as a digital ballpoint to capture the drawing data of the test subjects and thereby has limited applicability in practice. Furthermore, it may be too complicated for the test subjects who are illiterate or lacking formal education to perceive or draw a clock.

BRIEF SUMMARY OF THE INVENTION

There continues to be a need in the art for improved designs and techniques for a method for screening, diagnosing, or predicting presence, progression, or treatment effects of cognitive dysfunctions such as dementia based on drawing behavior changes.

Embodiments of the subject invention pertain to a method for collecting and analyzing drawing data and personal data of a test subject and predicting the probability that the test subject has a cognitive dysfunction based on a pre-trained Naïve Bayes model.

According to an embodiment of the subject invention, a first method for screening, diagnosing, or predicting presence, progression, or treatment effects of a cognitive dysfunction such as dementia based on analysis of drawing behavior changes by a pre-trained Naïve Bayes model is provided. The method can comprise steps of obtaining drawing data of at least one image created by a test subject on a digital device and personal data of the test subject; reconstructing the at least one image based on the drawing data obtained; converting the drawing data to drawing features comprising a plurality of motion features and a plurality of geometric features; and determining probability that the test subject has a cognitive dysfunction based on the drawing features and the personal data by a pre-trained Naïve Bayes model. Moreover, the obtaining the drawing data comprises obtaining the drawing data from both the at least one image created and the process of creating the at least one image. The at least one image is recorded in real time with a pixel level precision by the digital device. The drawing data can comprise continuous drawing trajectory including coordinates, time spent, and whether a point is an end of a touch on the digital device for each pixel drawn by the test subject. The at least one image comprises at least two interlocking pentagons. The personal data comprise information of age, gender, and education level of the test subject. The converting the drawing data to drawing features can comprise removing statistical outliers of the drawing data and then performing predefined mathematical formulas for obtaining the plurality of motion features and performing Principal Component Analysis (PCA) statistical procedures on the drawing data for obtaining the geometric features. The plurality of motion features can comprise at least one of summary statistics including mean and/or maximum and/or minimum and/or standard deviation and/or median of drawing time at a pixel or stroke or shape level, drawing distance at a pixel or stroke or shape level, stopping time at a shape level, or drawing speed at a pixel or stroke level. The plurality of geometric features can comprise at least one of a number of corners of the at least one image, a number of closed shapes of the at least one image. The converting the drawing data to the number of closed shapes of the plurality of geometric features can comprise following steps: filtering the drawing data based on instantaneous drawing speeds;

converting drawing data into a set of connected stokes by connecting any two pixels that are spaced apart from each other by a distance smaller than a threshold value; filtering the set of connected stokes into a polygon, if a starting point and an ending point of each connected stroke are spaced apart from each other by a distance smaller than the threshold value; and determining the number of closed shapes to be a number of group in the filtering the set of connected stokes into the polygon that has at least a predetermined number of connected strokes. Furthermore, the converting the drawing data to the number of corners of the plurality of geometric features can comprise following steps: filtering the drawing data based on instantaneous drawing speeds; converting drawing data into a set of connected stokes by connecting any two pixels that are spaced apart from each other by a distance smaller than a first threshold value; calculating a number of mid-points, if following condition satisfies: a sum of a distance between a starting point and a mid-point of connected stroke and an ending point and the mid-point of connected stroke is larger than a distance between the starting point and the ending point of connected stroke; and performing clustering if mid-points are spaced apart from each other by a distance smaller than a second threshold value. The reconstructing the image created comprises steps of filtering entire drawing trajectory of the at least one image to reassemble separated drawing segments; re-drawing the figure pixel by pixel based on the drawing segments obtained in the filtering and stored for processing; and resizing the image to a predetermined size and converting the image into greyscale. The cognitive dysfunction may include dementia.

In certain embodiment of the subject invention, a second method for developing a prediction model for screening, diagnosing, or predicting presence, progression, or treatment effects of a cognitive dysfunction such as dementia based on analysis of drawing behavior changes by a pre-trained Naïve Bayes model can comprise steps of: collecting personal data and drawing data of at least one image created by clinically diagnosed and/or screened subjects with the cognitive dysfunction and from subjects without the cognitive dysfunction; converting the drawing data to drawing features, comprising a plurality of motion features and a plurality of geometric features; reconstructing the at least one images based on the drawing data collected; performing Principal Component Analysis statistical procedures on the drawing data to obtain a plurality of extended geometric features and storing the obtained plurality of eigenvectors of the extended geometric features; selecting key motion features from the plurality of motion features by removing summary statistics with high correlation (>0.7), performing a group removal on each group of motion features, and removing motion features that are of similar clinical meaning; and developing a pre-trained model based on Naïve Bayes method with a greedy variable selection for performing on the motion features, the geometric features and the key motion features. The converting the drawing data to drawing features can comprise performing predefined mathematical formulas for obtaining the plurality of motion features and Principal Component Analysis (PCA) statistical procedures on the drawing data for obtaining the geometric features. The motion features can comprise at least one of summary statistics including mean and/or maximum and/or minimum and/or standard deviation and/or median of drawing time at a pixel or stroke or shape level, drawing distance at a pixel or stroke or shape level, stopping time at a shape level, or drawing speed at a pixel or stroke level. The plurality of geometric features can comprise at least one of a number of corners of the at least one image, a number of closed shapes of the at least one image, and a minimum distance between every two corners of the two closed shapes. Moreover, the Naïve Bayes method with a greedy variable selection can comprise steps of: starting with no drawing features in the model; at each step, adding one drawing feature to the model, in which the drawing feature brings the largest improvement to cross-validated Area Under Curve; stopping adding features when there is no improvement to the model; and fitting the selected drawing features with a pre-defined distribution and saving for prediction.

In another embodiment of the subject invention, a non-transitory computer-readable medium comprising program instructions stored thereon that, when executed, cause a processor to perform a method for screening, diagnosing, or predicting presence, progression, or treatment effects of a cognitive dysfunction such as dementia based on analysis of drawing behavior changes by a pre-trained Naïve Bayes model is provided. The method can comprise steps of obtaining drawing data of at least one image created by a test subject on a digital device and personal data of the test subject; reconstructing the at least one image based on the drawing data obtained; converting the drawing data to drawing features comprising a plurality of motion features and a plurality of geometric features; and determining probability that the test subject has a cognitive dysfunction based on the drawing features and the personal data by a pre-trained Naïve Bayes model.

In another embodiment of the subject invention, a non-transitory computer-readable medium comprising program instructions stored thereon that, when executed, cause a processor to perform a method for developing a prediction model for screening, diagnosing, or predicting presence, progression, or treatment effects of a cognitive dysfunction such as dementia based on analysis of drawing behavior changes by a pre-trained Naïve Bayes model is provided. The method can comprise steps of collecting personal data and drawing data of at least one image created by clinically diagnosed and/or screened subjects with the cognitive dysfunction and from subjects without the cognitive dysfunction; converting the drawing data to drawing features, comprising a plurality of motion features and a plurality of geometric features; reconstructing the at least one images based on the drawing data collected; performing Principal Component Analysis statistical procedures on the drawing data to obtain a plurality of extended geometric features and storing the obtained plurality of eigenvectors of the extended geometric features; selecting key motion features from the plurality of motion features by removing summary statistics with high correlation (>0.7), performing a group removal on each group of motion features, and removing motion features that are of similar clinical meaning; and developing a pre-trained model based on Naïve Bayes method with a greedy variable selection for performing on the motion features, geometric features and key motion features.

DETAILED DISCLOSURE OF THE INVENTION

Figure 1:
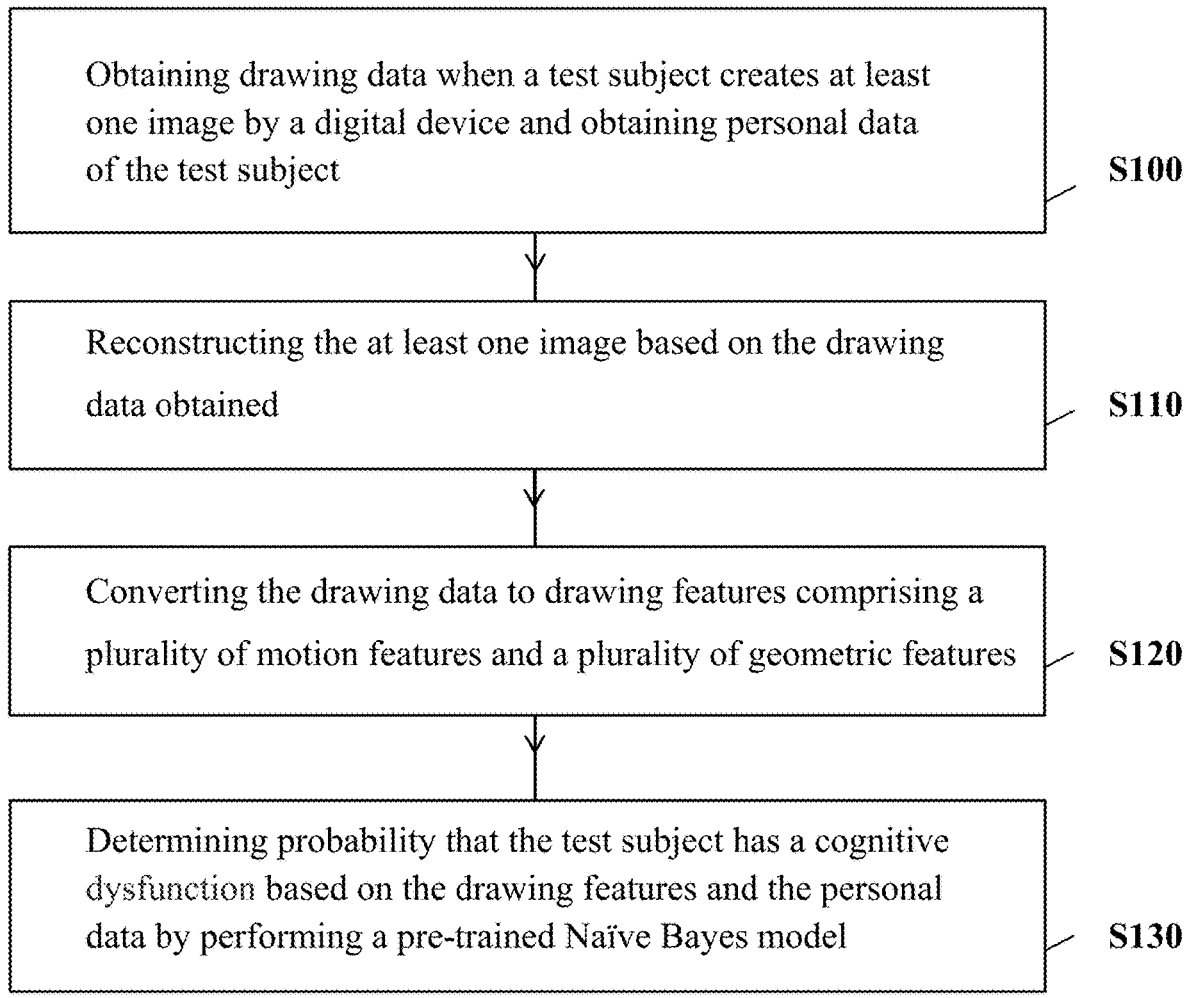
FIG. 1 is a flowchart diagram of a first method for screening, diagnosing, or predicting presence, progression, or treatment effects of cognitive dysfunctions based on an analysis of drawing behavior changes by a pre-trained Naïve Bayes model according to an embodiment of the subject invention.

Definition of Terms:
1. Motion features: a set of variables related to a drawing process.
2. A group of motion features: a set of variables including either summary statistics (mean and/or maximum and/or minimum and/or standard deviation and/or median) of drawing time at a pixel or stroke or pentagon level, drawing distance at a pixel or stroke or pentagon level, stopping time at a pentagon level, or drawing speeds at a pixel or stroke level.
3. Geometric features: a set of variables related to characteristics of a final image drawn.
4. img_1: a first Principal Component score obtained from the Principal Component Analysis for the final image drawn.
5. img_2: a second Principal Component score obtained from the Principal Component Analysis for the final image drawn.
6. img_3: a third Principal Component score obtained from the Principal Component Analysis for the final image drawn.
7. Extended geometric features: a set of variables generated from the geometric features and related to the characteristics of the final image drawn which may include img_1, img_2 and img_3.
8. Personal data: a set of variables that are related to the objective personal background of a test subject.
9. stfp: stopping time of drawing a first closed loop such as a pentagon.
10. stsp: stopping time of drawing a second closed loop such as a pentagon.
11. itfp: drawing time of the first closed loop such as a pentagon.
12. itsp: drawing time of the second closed loop such as a pentagon.
13. itp-avg: mean drawing time per pixel.
14. itp-max: maximum drawing time per pixel.
15. itp-med: median drawing time per pixel.
16. itp-std: standard deviation of drawing time per pixel.
17. its-avg: mean drawing time per stroke.
18. its-max: maximum drawing time per stroke.
19. its-min: minimum drawing time per stroke.
20. its-std: standard deviation of drawing time per stroke.
21. idfp: drawing distance of the first closed loop such as a pentagon.
22. idsp: drawing distance of the second closed loop such as a pentagon.
23. idp-avg: mean drawing distance in pixel scope.
24. idp-max: maximum drawing distance in pixel scope.
25. idp-med: minimum drawing distance in pixel scope.
26. idp-std: standard deviation of drawing distance in pixel scope.
27. ids-avg: average drawing distance in stroke scope.
28. ids-max: maximum drawing distance in stroke scope.
29. ids-min: minimum drawing distance in stroke scope.
30. ids-std: standard deviation of drawing distance in stroke scope.
31. dsp-avg: mean drawing speed in pixel scope.
32. dsp-med: median drawing speed in pixel scope.
33. dsp-max: maximum drawing speed in pixel scope.
34. dsp-std: standard deviation drawing speed in pixel scope.
35. dss-avg: mean drawing speed in stroke scope.
36. dss-min: minimum drawing speed in stroke scope.
37. dss-max: maximum drawing speed in stroke scope.
38. dss-std: standard deviation drawing speed in stroke scope.
39. ncorners: number of angles in the final image.
40. nclosures: number of polygons that are closed in the final image.

First Method

As illustrated in FIG. 1, a first method for screening, diagnosing, or predicting presence, progression, or treatment effects of cognitive dysfunctions such as dementia is based on an analysis of drawing behavior changes by a pre-trained Naïve Bayes model. The first method can comprise a step S100 of obtaining drawing data of at least one image created by a test subject on a digital device and obtaining personal data of the test subject, a step S110 of reconstructing the at least one image based on the drawing data obtained, a step S120 of converting the drawing data to drawing features comprising a plurality of motion features and a plurality of geometric features, and a step S130 of determining probability that the test subject has a cognitive dysfunction based on the drawing features and the personal data by performing the pre-trained Naïve Bayes model. The steps are explained in more details below.

Obtaining Drawing Data

At step S100, the test subject creates at least one image on a digital device and the drawing data of the at least one image created are recorded by the digital device or any suitable devices.

In one embodiment, the drawing data can be captured by a mobile application capable of running on an Android or an iOS platform having a touch screen. The test subject is required to copy a specific geometric object, such as a plurality of pentagons, shown on the touch screen by the application. For example, the drawing can be created with a canvas element in HTML and event listeners of touching and dragging in the touch screen are implemented to record the drawing behaviors of the test subject. Whenever the test subject touches the touch screen, the x and y coordinates and the timestamp of the touch are recorded in a form of a data array until the test subject touches a "submit" button on the touch screen. All drawing data recorded are then transmitted to an analysis module such as a backend server for storage and analysis. The application can be implemented to have a "undo" button on the touch screen through which the test subject can erase the drawing or redraw the at least one image. However, the example should not be construed as limiting.

Figure 2:
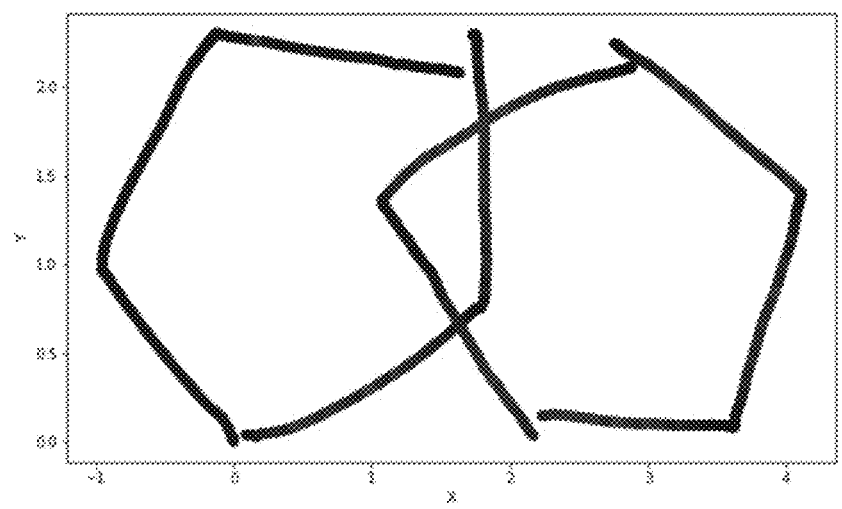
FIG. 2 shows an exemplary drawing created by a test subject on a digital device, according to an embodiment of the subject invention.

In one embodiment, the at least one image can comprise at least two interlocking pentagons as shown in FIG. 2 and the at least one image can be recorded in real time with a pixel level precision by the digital device. However, the example should not be construed as limiting.

Figure 3:
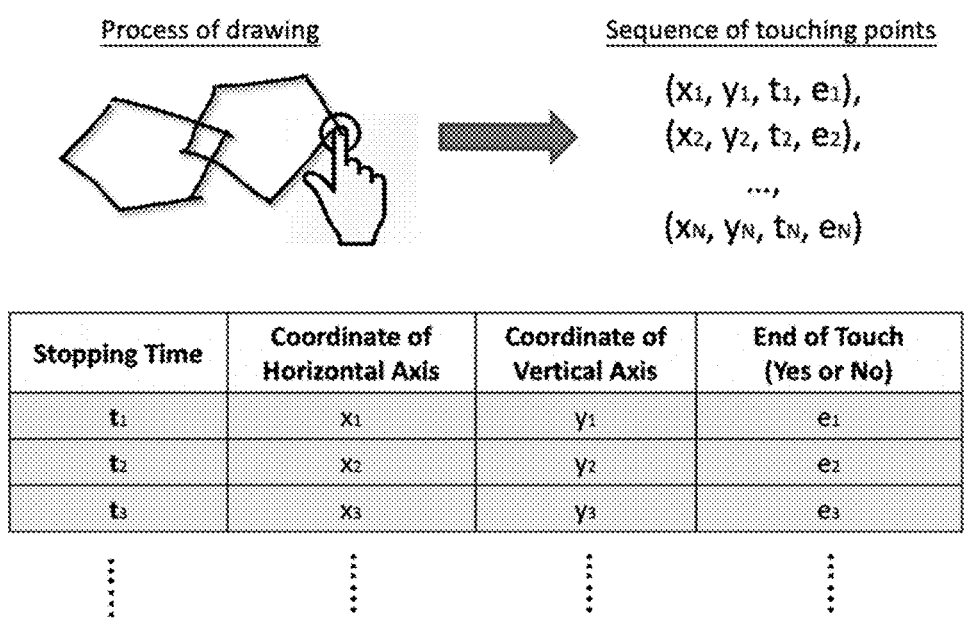
FIG. 3 shows extractions of drawing data obtained from the drawing processes of the test subject according to an embodiment of the subject invention.

It is noted that the drawing data obtained as described above can comprise both data depicting the at least one image created and data depicting the dynamic process of creating the at least one image. As illustrated in FIG. 3, for example, the drawing data can comprise continuous drawing trajectory including coordinates, time spent, and whether a point is an end of a touch on the digital device for each pixel drawn by the test subject.

Moreover, at step S100, the personal data of the test subject are also recorded by the digital device or any suitable devices. For example, the application can allow the test subject or another user to input personal data of the test subject including age, gender and educational level. However, the example should not be construed as limiting.

From epidemiology perspective, aging is the strongest risk factor associated with the risk of developing dementia as dementia is a disease related to frailty. Gender is another critical factor linked to some types of dementia. Thus, women are more likely to develop Alzheimer's disease than men due to the lack of the hormone estrogen after the menopause. For vascular dementia, men are at higher risk than women as men are more prone to heart diseases, which can cause vascular dementia. Therefore, personal data is essential in predicting the risks of afflicting cognitive dysfunctions such as dementia.

Reconstructing the Drawing

Figure 4:
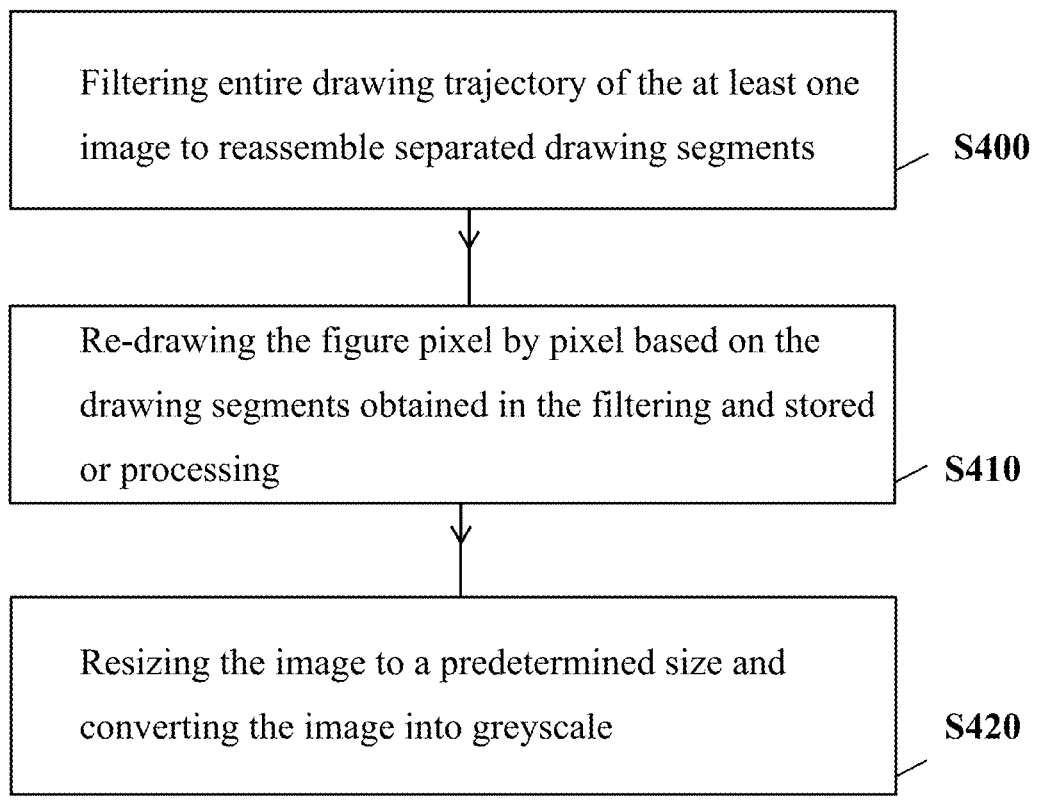
FIG. 4 is a flowchart diagram of steps of reconstructing the image created by the test subject according to an embodiment of the subject invention.

When the drawing data transmitted are received by the analysis module, the at least one image is reconstructed based on the drawing data and then undergoes image pre-processing. Referring to FIG. 4, the reconstructing can comprise a step S400 of filtering entire drawing trajectory of the at least one image to reassemble separated drawing segments, a step S410 of re-drawing the image pixel by pixel based on the drawing segments obtained in the filtering and stored for processing; and a step S420 of resizing the image to a predetermined size and converting the image into greyscale. For example, the image can be resized to a dimension of, for example, 56 pixel×56 pixel, and converted into greyscale. However, the example should not be construed as limiting.

Converting the Drawing Data to Drawing Features

At step S120 of FIG. 1, the drawing data are then converted to drawing features including a plurality of motion features and a plurality of geometric features. For the test subject denoted by S, the drawing process (S) is captured in real time and can be denoted by Equation (1):

$$(S) = [x_r, y_r, t_r, e_r)]_{r=1}^N = [s_1, \ldots s_L] \quad (1)$$

where $e_r$ is a binary indicator denoting whether the $r^{th}$ point is at end of a stroke, and $N = \Sigma_{i=1}^L M_i$ is a total number of points in pixel scope captured in the drawing process.

Therefore, by filtering $e_r$, as any change of value is an indication of a change in stroke, a sequence of strokes $[s_1, \ldots s_L]$ is generated, preserving the drawing order, while a stroke $s_m$ includes a sequence of points as denoted by Equation (2):

$$s_m = p_{i,1}, \ldots p_{i,M_i} \quad (2)$$

At each point $p_{i,j}$ there are three quantities: $(x_{i,j}, y_{i,j}, t_{i,j})$, where $x_{i,j}$ and $y_{i,j}$ correspond to the coordinates of the drawing point in pixel, and $t_{i,j} \in \mathbb{R}^+$ is the amount of time in seconds spent on the point $p_{i,j}$ before moving to the next point $p_{i,j+1}$.

Before calculating the geometric and motion features, (S) can be filtered to remove statistical outliers. A statistical outlier can be defined as any $p_{i,j}$ that has an instantaneous speed greater than a predetermined value, such as greater than 5 centimeter per millisecond. The unit of pixel can be converted to the unit of centimeter using the dot per inch of the digital device. These points are drawn mostly due to the mistouch of the screen by the test subject and thus it is beneficial to remove the outliers before generating the geometric and motion features. Thereafter, $s_m$ is smoothened to become a line by connecting the $p_{i,j}$ and the $p_{i+1,j+1}$ when a distance between the $p_{i,j}$ and the $p_{i+1,j+1}$ is smaller than a threshold value.

Figure 5:
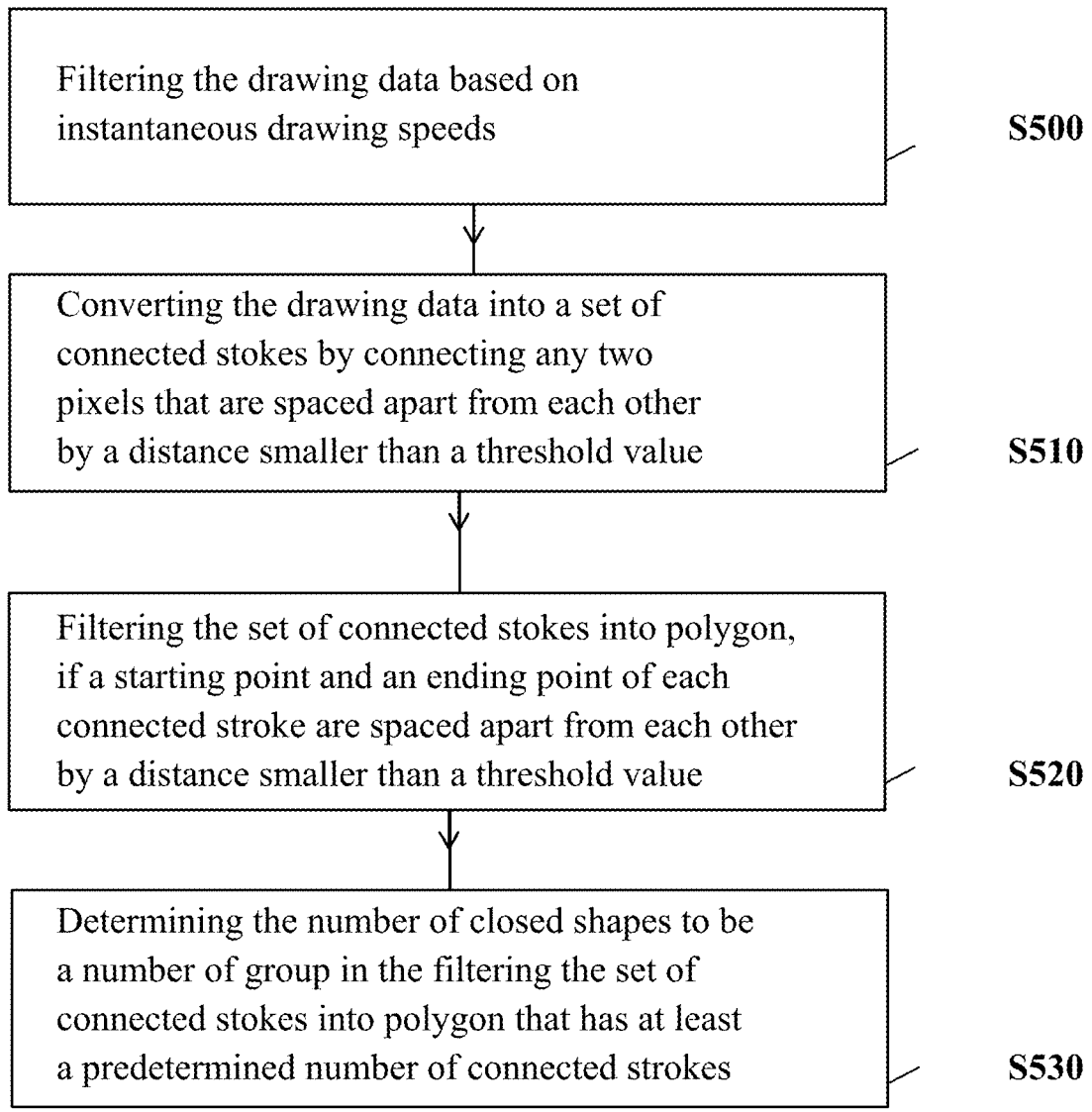
FIG. 5 is a flowchart diagram of steps of determining a number of closed shapes such as pentagons of the plurality of geometric features according to an embodiment of the subject invention.

Referring to FIG. 5, in one embodiment, determining a number of closed shapes such as pentagons of the plurality of geometric features can comprise a step S500 of filtering the drawing data based on instantaneous drawing speeds; a step S510 of converting the drawing data into a set of connected stokes by connecting any two pixels that are spaced apart from each other by a distance smaller than a threshold value; a step S520 of, if a starting point and an ending point of each connected stroke are spaced apart from each other by a distance smaller than a threshold value, filtering the set of connected stokes into a polygon; and a step S530 of determining the number of closed shapes such as pentagons to be a number of groups in the filtering the set of connected stokes into a polygon that has at least a predetermined number of connected strokes.

In one embodiment, to calculate the geometric feature nclosures, if the start point or the end point of a stroke s and the start point or end point of another stroke are spaced apart from each other by a distance smaller than a threshold value, the strokes are determined to be connected to form a set of connected strokes. The nclosures is thereby defined as a number of the set of connected strokes where the start point and the end point of the set of connect strokes are spaced apart from each other by a distance smaller than the threshold value, forming a close loop.

Figure 6:
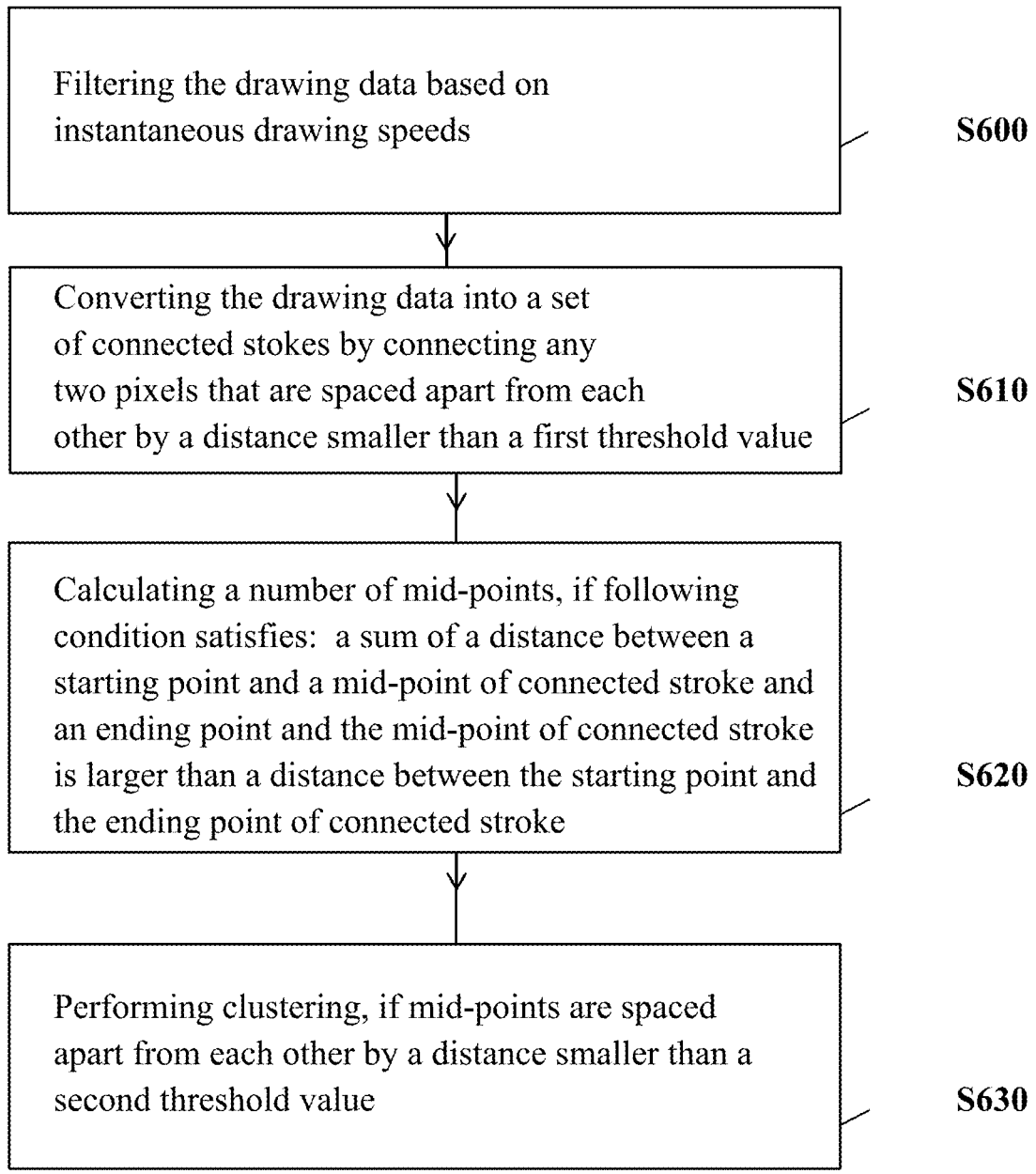
FIG. 6 is a flowchart diagram of steps of determining a number of corners of a plurality of geometric features according to an embodiment of the subject invention.

As illustrated in FIG. 6, determining a number of corners of a plurality of geometric features can comprise a step S600 of filtering the drawing data based on instantaneous drawing speeds; a step S610 of converting the drawing data into a set of connected stokes by connecting any two pixels that are spaced apart from each other by a distance smaller than a first threshold value; a step S620 of, if following condition satisfies: a sum of a distance between a starting point and a mid-point of connected stroke and an ending point and the mid-point of connected stroke is larger than a distance between the starting point and the ending point of connected stroke, calculating a number of mid-points; and a step S630 of, if mid-points are spaced apart from each other by a distance smaller than a second threshold value, performing clustering.

Figure 17:
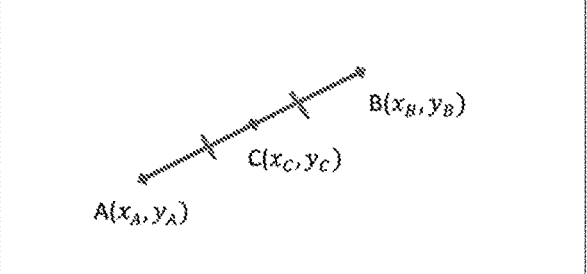
FIG. 17 is an example showing how to distinguish a corner.

In one embodiment, a pentagon is defined as a shape of a polygon having five connected strokes. FIG. 17 below is an example showing how to distinguish a corner in the drawing. For every stroke $s_m$ in $[s_1 \ldots s_L]$ denoted in FIG. 17, A, B is the start point and the end point, respectively. In one instance, there exists a point C where AC=CB. In another instance, if there exists a point C where AC+CB>AB, the point C is determined to be a corner. Otherwise, the point C is determined to be not a corner. The corners that are close together and spaced apart from each other by a distance smaller than a threshold value are filterer out by means of clustering as a round corner that would be miscalculated as many corners. The ncorners is defined as a number of corners in $[s_1, \ldots s_L]$.

Moreover, a plurality of extended geometric features can be extracted from the geometric features by a Principal Component Analysis (PCA) method on the final image after rescaling and converted into grey scale from the set of connected strokes. The eigenvalues are then saved for prediction.

In one embodiment, the motion features can be calculated in terms of pixel, stroke and closed loop/pentagon scope. The main motion feature can include, for example, the drawing time, the stopping time, the drawing distance and the drawing speed. The drawing time is defined as the time spent when the test subject touches the touch screen of the digital device. The drawing distance is defined as the distance along which the test subject's touch moves on the touch screen of the digital device. The stopping time is defined as the time spent when the test subject does not touch the touch screen of the digital device. The drawing speed is defined as the distance over time when the test subject touches the touch screen of the digital device. Summary statistics can include mean and/or median and/or maximum and/or minimum and/or standard deviation calculated for each main motion feature as shown in Table 2 and Table 3 below.

TABLE 2

Motion features in pentagon level

| Statistics for each pentagon | For first pentagon | For second pentagon |
| --- | --- | --- |
| Drawing Time | itfp | itsp |
| Stopping Time | stfp | stsp |
| Drawing Distance | idfp | idsp |

TABLE 3

Motion features in pixel and stroke level

| | For each pixel (mean and/or maximum and/or median and/or standard deviation) | For each stroke (maximum and/or minimum and/or mean and/or standard deviation) |
| --- | --- | --- |
| Summary Statistics | | |
| Drawing Time | itp-avg, itp-max, itp-med, itp-std | Its-avg, its-max, its-min, its-std, |
| Drawing Distance | idp-avg, idp-max, idp-med, idp-std, | ids-avg, ids-max, ids-min, ids-std, |
| Drawing Speed | dsp-avg, dsp-med, dsp-max, dsp-std | dss-avg, dss-min, dss-max, dss-std |

Motion features Selection

After personal data, motion features, geometric features and extended geometric features are obtained as described above, simplification of the motion features is performed before the prediction model is developed.

With a greater number of motion features, a greater number of samples needed to represent the same combination of motion features value in the data set. When the number of motion features increases, the prediction model developed becomes more complex and has a higher chance of overfitting, resulting in poor performance for prediction on real data. Thus, the motion features obtained are selected into a smaller group including fewer motion features.

To simplify the motion features, variables with higher correlation (for example, a correlation >0.7) within a group of motion features are removed. Then, a group removal is performed among groups of motion features. The group of motion features which has high correlation with another group is removed, in which any element of the group has correlation >0.7 with an element of another group. Finally, the motion features that are of similar clinical meaning are removed.

Naïve Bayes Model with a Greedy Feature Selection

At step S130 of FIG. 1, the probability that the test subject has a cognitive dysfunction such as dementia can be determining based on the drawing features and the personal data by a pre-trained Naïve Bayes model as a baseline prediction model.

The Naïve Bayes model places some prior distribution on the features and computes the posterior probability of P(Y|X), where Y is the state of having dementia and X is the set of features containing personal data, motion features and geometric features. It implicitly assumes that the features are independent.

In one embodiment, following prior distributions are placed on the features:
1. If the feature is nominal, a multinomial distribution is placed as the prior.
2. If the feature is continuous, a normal distribution is placed as the prior.
3. If the feature is binary, a normal binomial is placed as the prior.

However, Naïve Bayes model does not naturally select any important features, since all the input features are treated equally. Therefore, a variable selection technique is applied to first identify the important features and then use these important features as the input to the model. A greedy feature selection method, similar to the forward stepwise selection method, is applied to select the important features.

Figure 8:
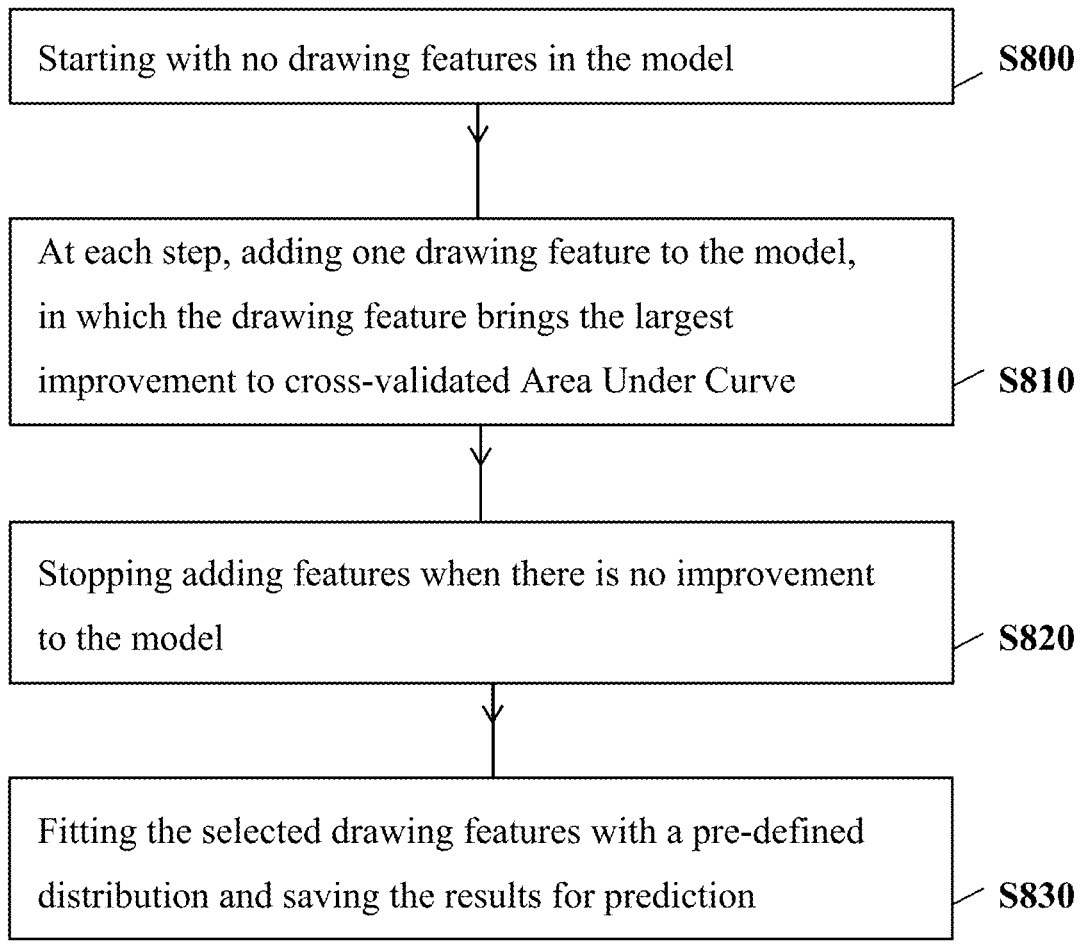
FIG. 8 is a flowchart diagram of the Naïve Bayes model with a greedy variable selection according to an embodiment of the subject invention.

Referring to FIG. 8, the Naïve Bayes model with a greedy variable selection can comprise a step S800 of starting with no drawing features in the model, a step S810 of at each step, adding one drawing feature to the model, in which the drawing feature brings the largest improvement to the cross-validated Area Under Curve, a step S820 of stopping adding features when there is no improvement to the model, and a step S830 of fitting the selected drawing features with a pre-defined distribution and saving the results for prediction. The set of important features selected are the input to the Naïve Bayes model.

A nested cross-validation approach is utilized to evaluate the performance of the Naïve Bayes model, with 10-folds for the inner loop and 20-folds for the outer loop. The inner loop is for the greedy variable selection and will result in a set of important features. The outer loop is for computing the evaluation metric.

In certain embodiment, a non-transitory computer-readable medium can comprise program instructions stored thereon that, when executed, cause a processor to perform the first method for screening, diagnosing, or predicting presence, progression, or treatment effects of cognitive dysfunctions based on an analysis of drawing behavior changes, comprising steps of obtaining drawing data of at least one image created by a test subject on a digital device and personal data of the test subject; reconstructing the at least one image based on the drawing data obtained; converting the drawing data to drawing features comprising a plurality of motion features and a plurality of geometric features; and determining probability that the test subject has a cognitive dysfunction based on the drawing features and the personal data by a pre-trained Naïve Bayes model.

Second Method

Figure 7:
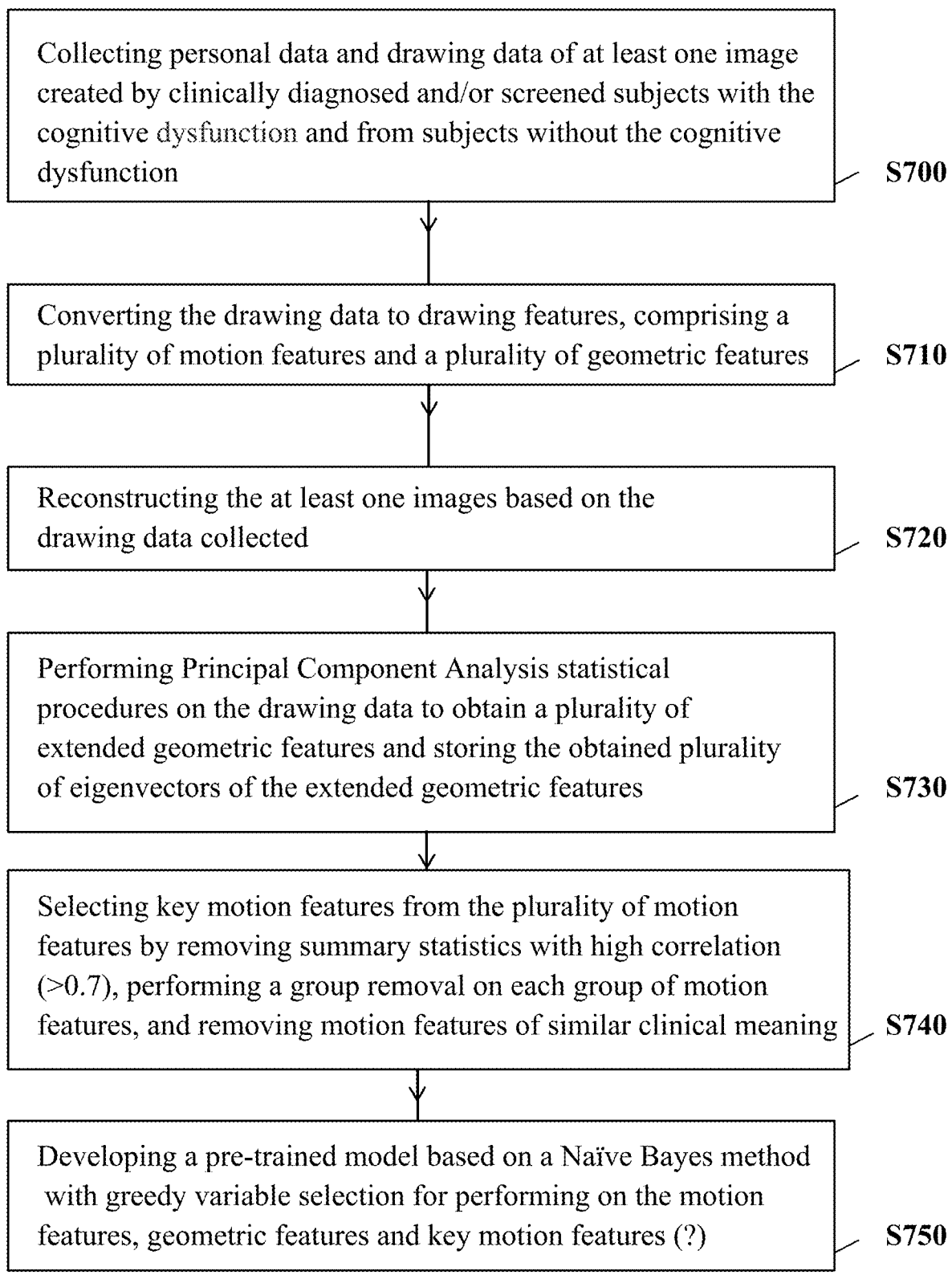
FIG. 7 is a flowchart diagram of a second method for screening, diagnosing, or predicting presence, progression, or treatment effects of cognitive dysfunctions based on an analysis of drawing behavior changes by a pre-trained Naïve Bayes model according to an embodiment of the subject invention.

FIG. 7 shows a flowchart of a second method for screening, diagnosing, or predicting presence, progression, or treatment effects of cognitive dysfunctions such as dementia based on an analysis of drawing behavior changes by a pre-trained Naïve Bayes model. The second method can comprise a step S700 of collecting personal data and drawing data of at least one image created by clinically diagnosed and/or screened test subjects with the cognitive dysfunction and from test subjects without the cognitive dysfunction, a step S710 of converting the drawing data to drawing features, comprising a plurality of motion features and a plurality of geometric features, a step S720 of reconstructing the at least one images based on the drawing data collected; a step S730 of performing Principal Component Analysis (PCA) statistical procedures on the drawing data to obtain a plurality of extended geometric features and storing the obtained plurality of eigenvectors of the extended geometric features, a step S740 of selecting key motion features from the plurality of motion features by removing summary statistics with high correlation (>0.7) and performing a group removal on each group of motion features, and removing motion features that are of similar clinical meaning; and a step S750 of developing a pre-trained model based on a Naïve Bayes method with a greedy variable selection for performing on the motion features, the geometric features, the extended geometric features, and the key motion features.

In certain embodiment, a non-transitory computer-readable medium comprising program instructions stored thereon that, when executed, cause a processor to perform the second method for developing a prediction model for screening, diagnosing, or predicting presence, progression, or treatment effects of a cognitive dysfunction based on an analysis of drawing behavior changes, comprising steps of collecting personal data and drawing data of at least one image created by clinically diagnosed and/or screened test subjects with the cognitive dysfunction and from test subjects without the cognitive dysfunction; converting the drawing data to drawing features, comprising a plurality of motion features and a plurality of geometric features; reconstructing the at least one images based on the drawing data collected; performing Principal Component Analysis statistical procedures on the drawing data to obtain a plurality of extended geometric features and storing the obtained plurality of eigenvectors of the extended geometric features; selecting key motion features from the plurality of motion features by removing summary statistics with high correlation (>0.7) and performing a group removal on each group of motion features, and removing motion features that are of similar clinical meaning; and developing a pre-trained model based on a Naïve Bayes method with a greedy variable selection for performing on the motion features, the geometric features, the extended geometric features, and the key motion features.

Figure 9:
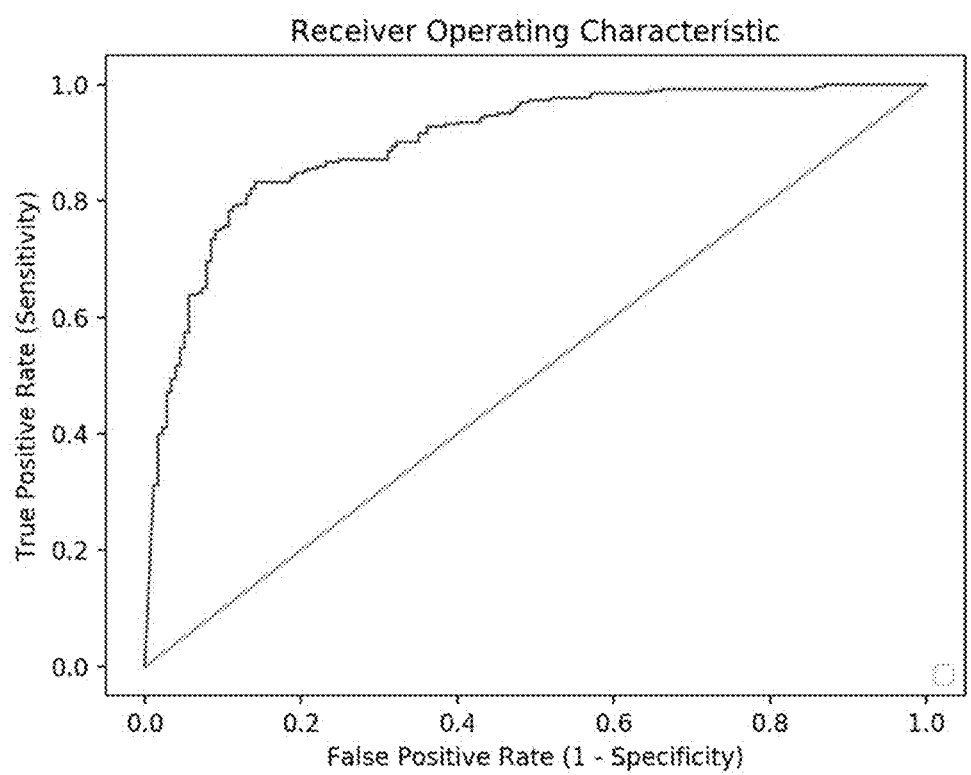
FIG. 9 shows a receiver operating characteristic (ROC) analysis based on the pre-trained Naïve Bayes prediction model according to an embodiment of the subject invention.

Referring to FIG. 9, a receiver operating characteristic (ROC) analysis based on the pre-trained Naïve Bayes prediction model is shown.

Figure 10A:
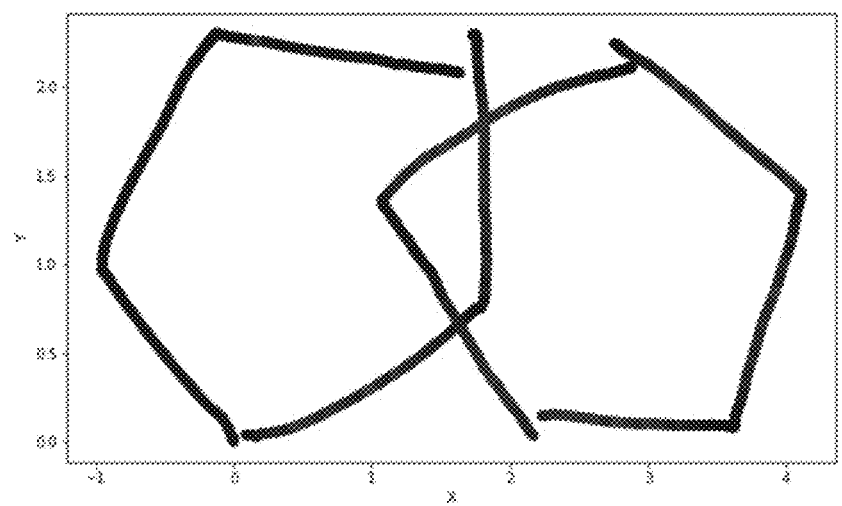
FIG. 10A shows an exemplary drawing of a test subject with dementia according to an embodiment of the subject invention.
Figure 10B:
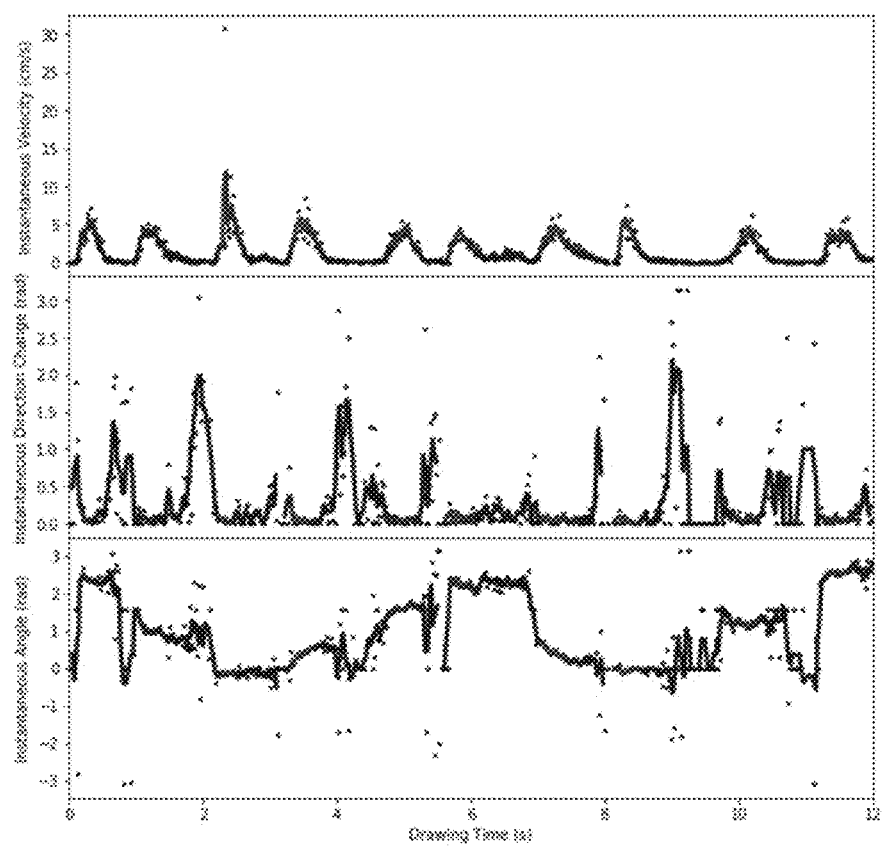
FIG. 10B shows exemplary analysis results of the drawing process of the test subject with dementia of FIG. 10A, according to an embodiment of the subject invention.

Moreover, FIG. 10A shows an exemplary drawing of a test subject with dementia and FIG. 10B shows exemplary analysis results of the drawing process of the drawing of the test subject with dementia of FIG. 10A according to an embodiment of the subject invention.

Figure 11A:
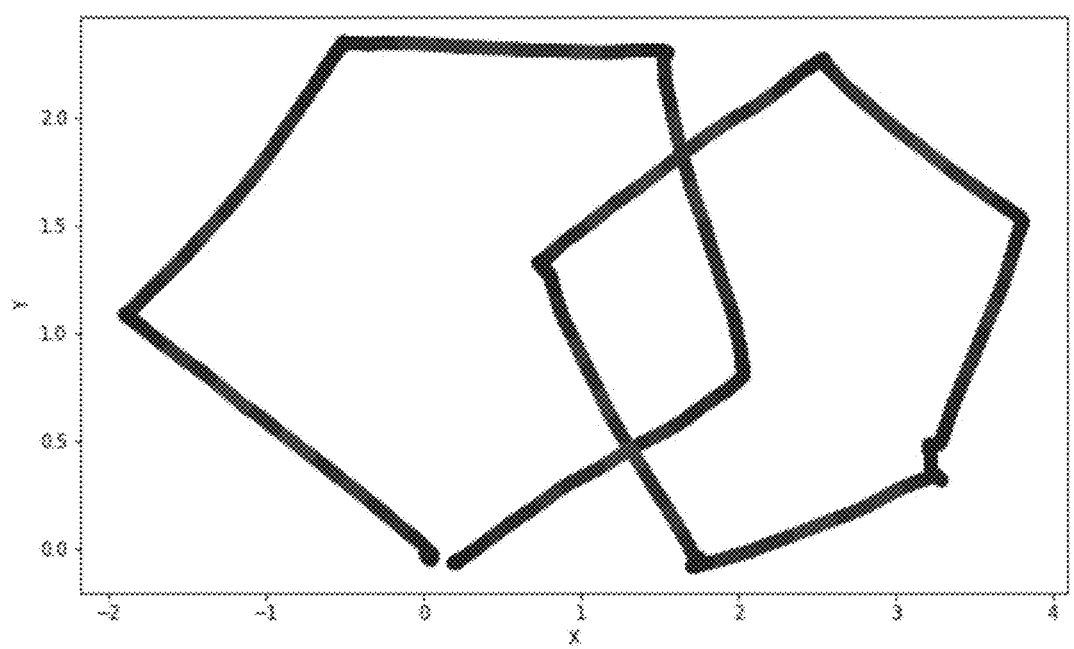
FIG. 11A shows exemplary drawing of a test subject without dementia according to an embodiment of the subject invention.
Figure 11B:
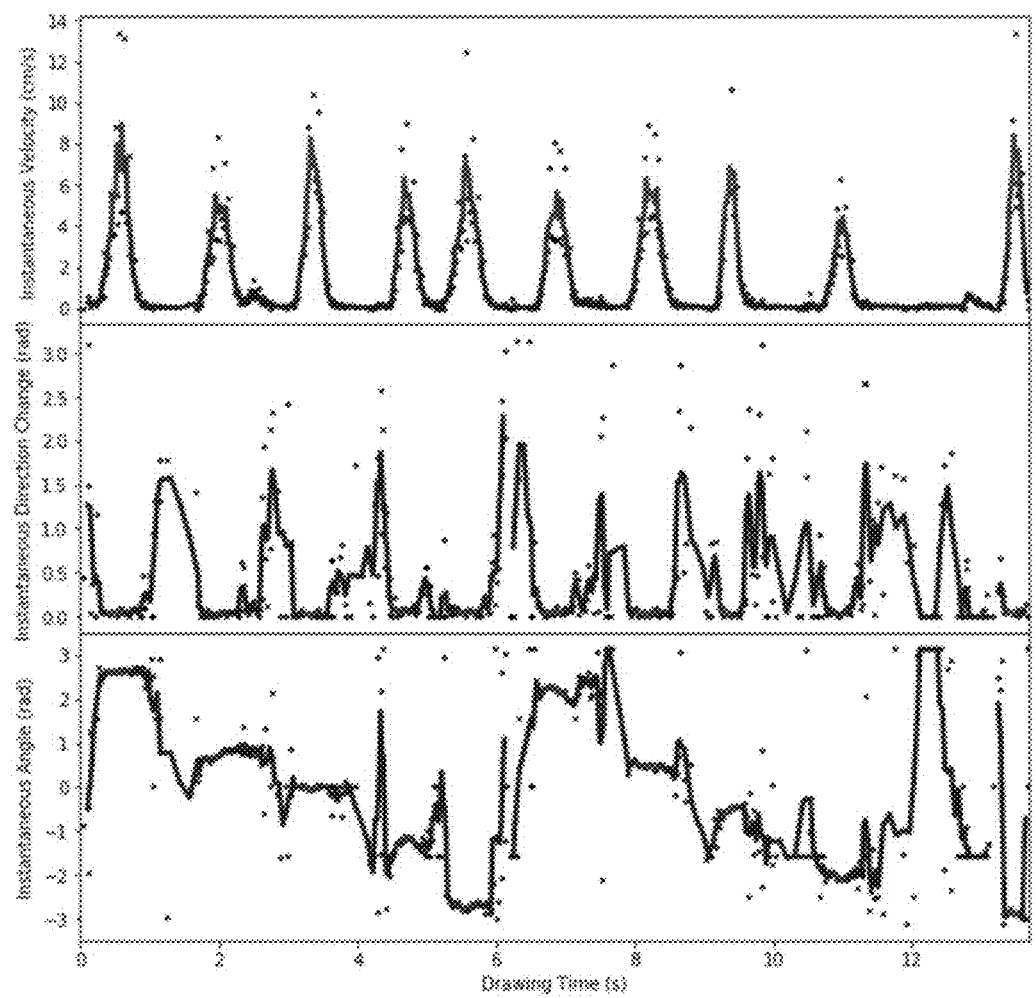
FIG. 11B shows exemplary analysis results of the drawing process of the test subject without dementia of FIG. 11A, according to an embodiment of the subject invention.

In contrast, FIG. 11A shows exemplary drawing of a test subject without dementia and FIG. 11B shows exemplary analysis results of the drawing process of the drawing of the test subject without dementia of FIG. 11A according to an embodiment of the subject invention.

Example: Clinical Studies

The Test Subject Inclusion Criteria for the Clinical Studies Include:
1. age 60 or above, and
2. native Cantonese speaker The Test Subject Exclusion Criteria for the Clinical Studies Include:
1. participants with concurrent cerebrovascular diseases,
2. participants with visual impairment,
3. a dementia patient with a Montreal Cognitive Assessment (MoCA) score ≤19, and
4. a healthy test subject with MoCA score <22.

Test Subjects Recruitment Process

Figure 12:
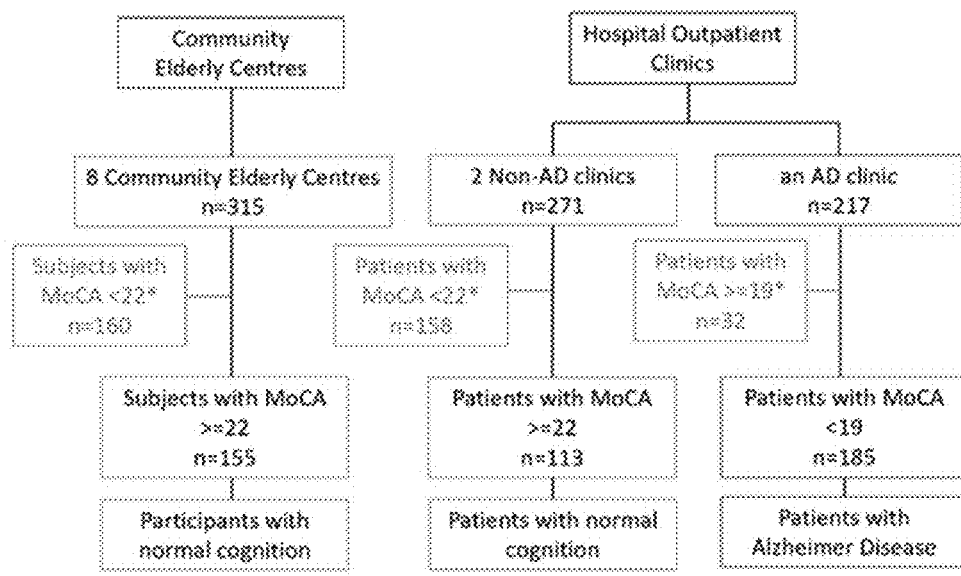
FIG. 12 is a flowchart diagram of a test subject recruitment process of a clinical study according to an embodiment of the subject invention.

268 Healthy controls (HCs) test subjects who are healthy and 185 test subject who are Alzheimer's disease (AD) patients were recruited between Jul. 1, 2016 and Jul. 31, 2018 as shown in FIG. 12. The AD test subjects were recruited in a geriatric research clinic in the Prince of Wales Hospital (PWH), Hong Kong. HCs test subjects were recruited in a neurology research clinic in the PWH, and eight community centers across Hong Kong. HCs test subjects were also recruited from the Mr Os. and Ms Os. Cohort in the Jockey Club Center for Osteoporosis Care and Control, the Chinese University of Hong Kong. The Mr Os. and Ms Os. is the largest cohort study that focuses on osteoporosis in the elders in Asia. The study was approved by the Survey and Behavioral Research Ethic Committee of the Chinese University of Hong Kong. Informed consent was provided to the test subjects prior to their participation in the clinical study.

Data Collection

Demographics such as age, education level and gender were extracted from all test subjects. All AD test subjects were clinically diagnosed by geriatrician using the Diagnostic and Statistical Manual of Mental Disorders (DSM-IV) diagnostic criteria. All test subjects were administrated with the MoCA by trained research staff. The Hong Kong version of MoCA was used, with the optimal local cutoff of 22/21. After the administration of MoCA, test subjects were provided with a figure of interlocking pentagons. They were asked to copy the figure on a digital drawing platform. The drawing platform was pre-installed on a smart tablet. There was no limit on the drawing time and the number of attempts. The characteristics of the test subjects of the clinical study are shown in Table 4.

Motion Feature Selection

Figure 13:
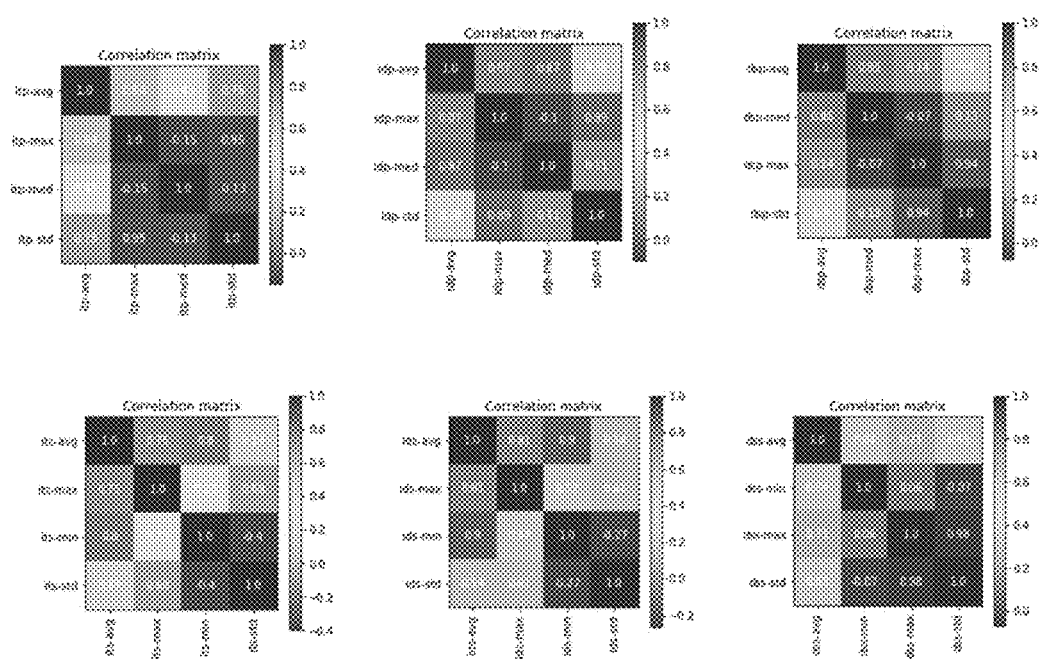
FIG. 13 shows a correlation matrix of each set of motion features of the clinical study according to an embodiment of the subject invention.

Within each set of motion features, for example, mean, max, median, standard deviation of drawing time was considered as one set, the summary statistics with a high correlation (for example, >0.7) were removed. The selected features are shown in Table 5 and a correlation matrix of each set of motion features is shown in FIG. 13.

TABLE 5

Selected features after step 1
Step 1: Choice of the remaining features

| | |
|---|---|
| itp | med, std |
| its | avg, std |
| idp | med, std |
| ids | avg, std |
| dsp | med, std |
| dss | min, std |

Figure 14:
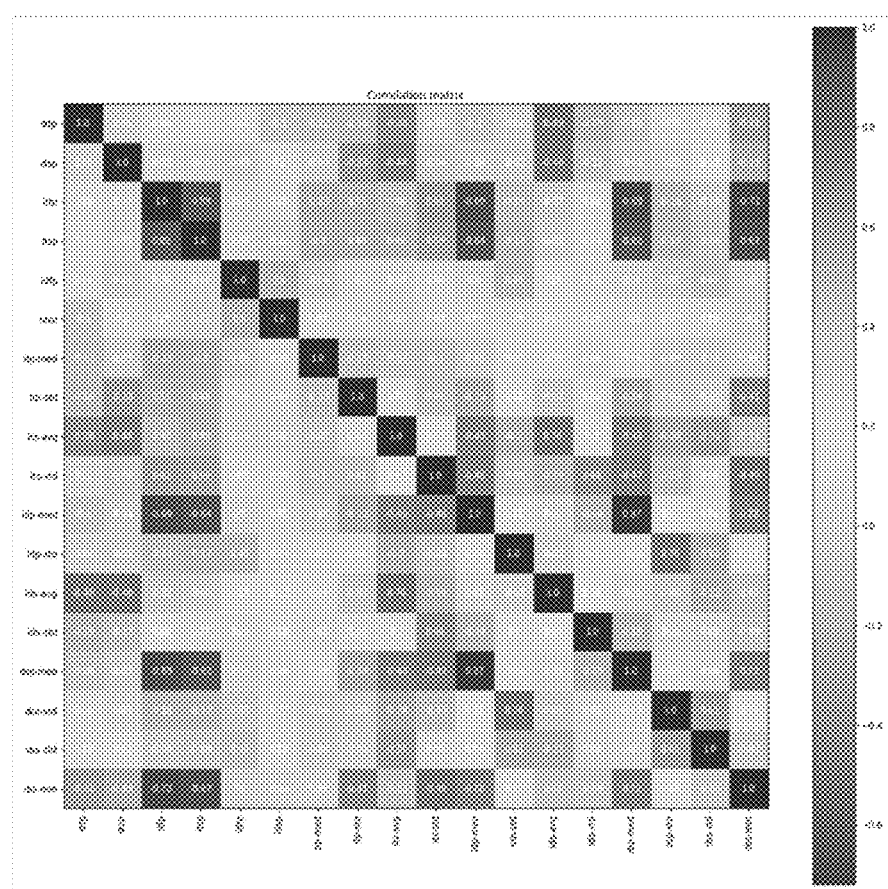
FIG. 14 shows a correlation matrix between feature groups of the clinical study according to an embodiment of the subject invention.

A group removal was perform on each group of motion features (for example, the median and standard deviation of itp are viewed as one group). The feature group which has high correlation with another group (in which any element of the group has a correlation >0.7 with an element of the another group) was removed. A correlation matrix between feature groups is shown in FIG. 14. The motion features including itsp, its, idp and dss were removed; while the motion features including stfp, stsp, itfp, idfp, idsp, itp-med, itp-std, ids-avg, ids-std, dsp-med and dsp-std were selected.

TABLE 4

Characteristics of the test subjects of the clinical study

| | Subjects with Normal Cognition | | | Patients with AD | |
|---|---|---|---|---|---|
| | Community Centres (n = 155) | Non-AD clinics (n = 113) | P-value* | AD clinic (n = 185) | P-value# |
| Age, years (mean, SD) | 72.21 (7.25) | 79.92 (5.87) | <0.001 | 80.33 (6.07) | <0.001 |
| Age, years (n, %) | | | | | |
| 60-69 | 68 (43.87%) | 4 (3.54%) | <0.001 | 8 (4.32%) | <0.01 |
| 70-79 | 57 (36.77%) | 42 (37.17%) | | 61 (32.97%) | |
| 80+ | 30 (19.35) | 67 (59.29%) | | 116 (62.70%) | |
| Sex, male (n, %) | 32 (20.64%) | 55 (48.67%) | <0.001 | 55 (29.73%) | 0.36 |
| Education, year (mean, SD) | 7.24 (4.49) | 9.49 (5.01) | <0.001 | 4.23 (4.25) | <0.001 |
| Education level (n, %) | | | | | |
| No official education | 6 (3.87%) | 7 (6.19%) | <0.001 | 43 (%) | <0.01 |
| Primary School | 85 (54.84%) | 25 (22.12%) | | 111 (%) | |
| Secondary School | 46 (29.68%) | 50 (44.25%) | | 23 (%) | |
| University | 18 (11.61%) | 31 (27.43%) | | 9 (%) | |
| Mean MoCA score (mean, SD) | 25.68 (2.21) | 24.41 (1.88) | <0.001 | 11.24 (4.11) | <0.001 |
| Visuospatial/executive | 4.00 (0.99) | 3.67 (1.06) | <0.05 | 1.18 (1.07) | <0.001 |
| Naming | 2.68 (0.56) | 2.73 (0.50) | 0.62 | 0.56 (1.05) | <0.001 |
| Attention | 5.50 (0.66) | 5.60 (0.59) | 0.17 | 3.25 (1.49) | <0.001 |
| Language | 2.94 (0.23) | 2.83 (0.38) | <0.01 | 2.04 (0.61) | <0.001 |
| Abstraction | 0.97 (0.71) | 0.66 (0.69) | <0.001 | 0.22 (0.44) | <0.001 |
| Memory | 3.10 (1.40) | 2.69 (1.37) | <0.01 | 0.04 (0.23) | <0.001 |
| Orientation | 5.89 (0.31) | 5.89 (0.31) | 0.89 | 2.07 (1.66) | <0.001 |

Figure 15:
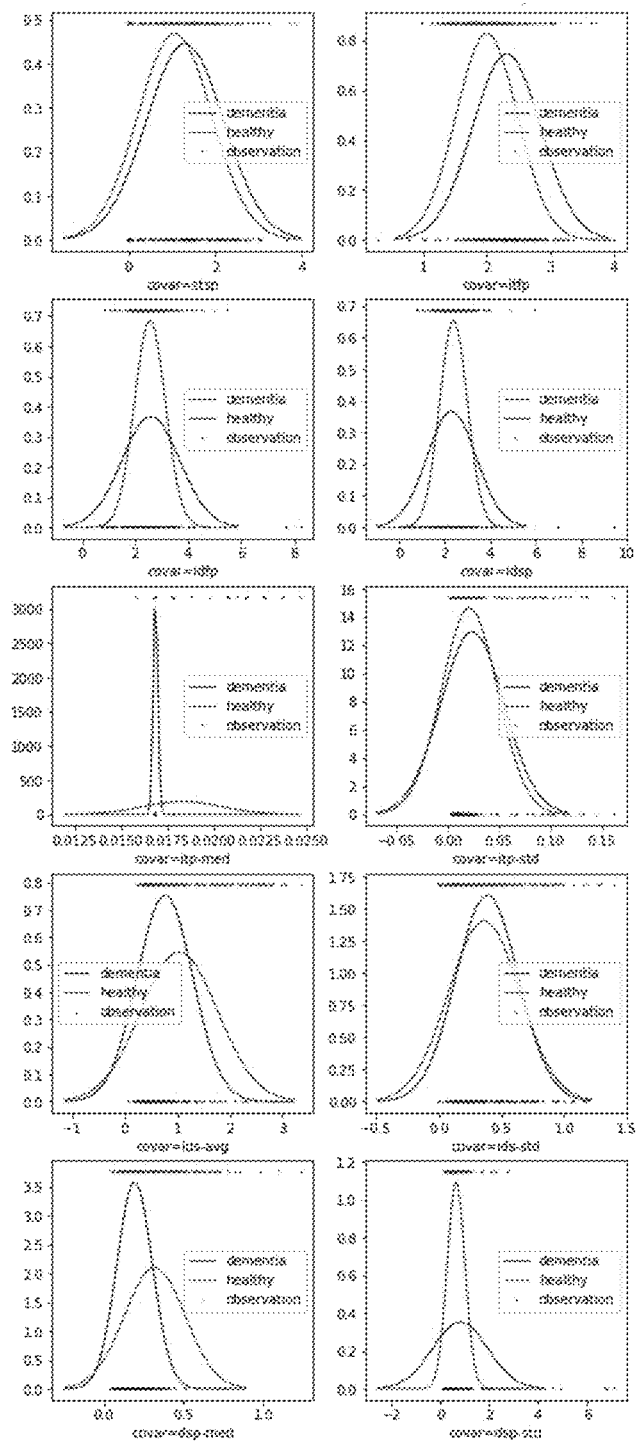
FIG. 15 shows distributions of the selected motion features in Healthy controls (HCs) test subject group and Alzheimer's disease (AD) test subject group after step 2 of the clinical study, according to an embodiment of the subject invention.

*Test subjects from community center vs test subjects from non-AD clinics; # AD patients vs all HCs FIG. 15 shows the distribution of the selected motion features in the HCs group and the AD group with the interpretation in Table 6.

TABLE 6

Explanation of the selected motion features
in the HCs group and the AD group

| Selected features | Interpretation (based on visualization) |
|---|---|
| stfp | Healthy people tend to have smaller stopping time when drawing the first pentagon |
| stsp | Healthy people tend to have smaller stopping time when drawing the second pentagon |
| itfp | Healthy people tend to have smaller drawing time of first pentagon |
| idfp | Drawing distance of first pentagon by the healthy people is more concentrated |
| idsp | Drawing distance of second pentagon by the healthy people is more concentrated |
| itp-med | People with dementia tend to have smaller (median) drawing time per point |
| itp-std | Not distinguishable for two groups |
| ids-avg | Healthy people tend to have longer drawing distance per stroke on average |
| ids-std | Healthy people tend to have smaller variance on drawing distance per stroke |
| dsp-med | Healthy people tend to have higher (median) drawing speed per point |
| dsp-std | Healthy people tend to have smaller variance on drawing speed per point |

Figure 16:
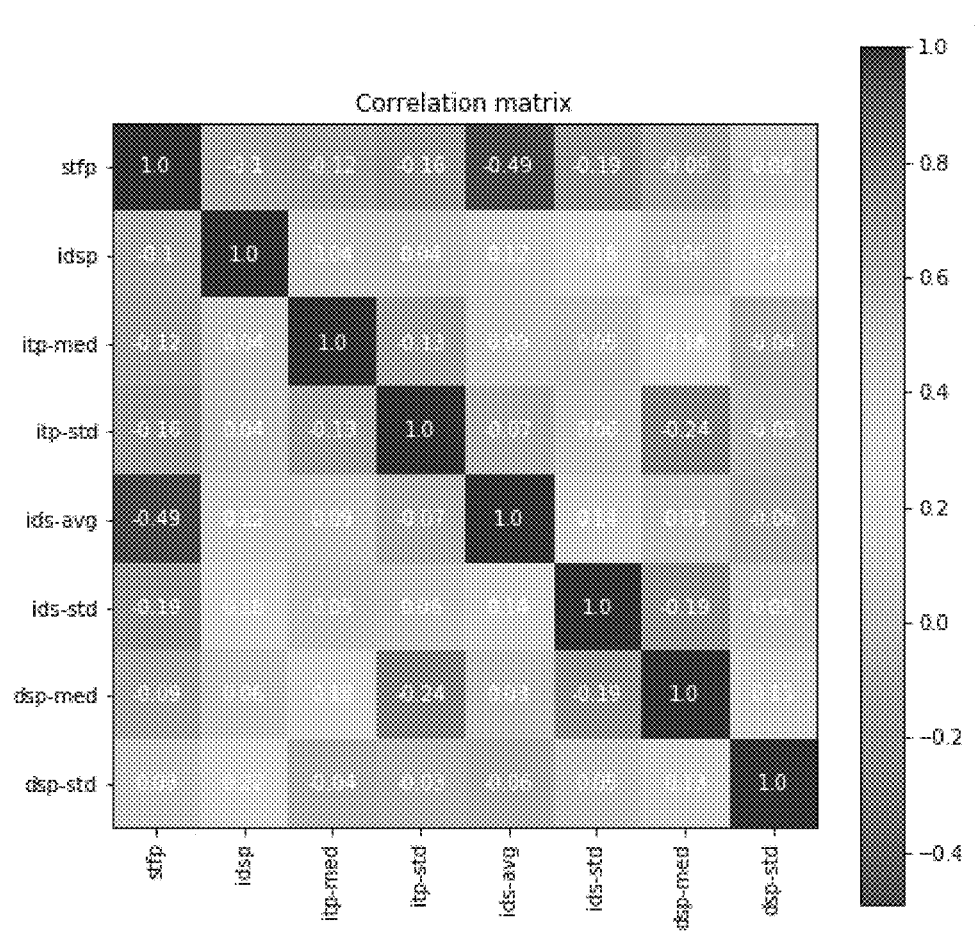
FIG. 16 shows a correlation matrix of final selected motion features of the clinical study according to an embodiment of the subject invention.

Features that are of similar clinical meaning were removed. For each group of variables in Table 7 with similar clinical meaning, either one of them was removed and the change was analyzed in cross-validated AUC in 5 separate models as shown in Table 8. The motion features including stsp, idfp and itfp were removed as a result. The selected motion features to enter final model included stfp, idsp, itp-med, itp-std, ids-avg, ids-std, dsp-med and dsp-std. A correlation matrix of the final selected motion features is shown in FIG. 16.

TABLE 7

The group of variables with similar clinical meaning

| Group | Variables with similar meaning | | Similarity in clinical meaning |
|---|---|---|---|
| 1 | stfp | stsp | Stopping time for different pentagon |
| 2 | stfp | idsp | Drawing distance for different pentagon |
| 3 | stfp | itfp | Drawing Time vs Stopping Time |
| 4 | From Group 1, 2, 3, remove 1 variable from each group (including stfp) | | |
| 5 | From group 1, 2, 3, remove 1 variable from each group (not including stfp) | | |

TABLE 8

Model performances after removing feature
with similar clinical meaning

| | Model 1A (remove stfp) | Model 1B (remove stsp) |
|---|---|---|
| Sensitivity | 0.772 | 0.740 |
| Specificity | 0.836 | 0.881 |
| Accuracy | 0.804 | 0.809 |
| AUC | 0.866 | 0.872 |

TABLE 8-continued

Model performances after removing feature
with similar clinical meaning

| | Model 2A (remove idfp) | Model 2B (remove idsp) |
|---|---|---|
| Sensitivity | 0.783 | 0.780 |
| Specificity | 0.819 | 0.836 |
| Accuracy | 0.801 | 0.808 |
| AUC | 0.873 | 0.873 |

| | Model 3A (remove stfp) | Model 3B (remove itfp) |
|---|---|---|
| Sensitivity | 0.772 | 0.775 |
| Specificity | 0.836 | 0.836 |
| Accuracy | 0.804 | 0.806 |
| AUC | 0.866 | 0.873 |

| | Model 4 (remove stfp, idsp) | Model 5 (remove stsp, idip, itfp) |
|---|---|---|
| Sensitivity | 0.775 | 0.715 |
| Specificity | 0.830 | 0.892 |
| Accuracy | 0.803 | 0.804 |
| AUC | 0.867 | 0.873 |

Naïve Bayes Model with a Greedy Feature Selection

The results of a 20-fold cross validation are shown in Table 9.

TABLE 9

The result of each cross validation of Naïve Bayes algorithm

| Times | AUC | Sensitivity | Specificity | Feature Selected |
|---|---|---|---|---|
| 1 | 0.91 | 0.8048 | 0.8771 | 'img_3', 'itp-med', 'dsp-med', 'ncorners', 'img_1', 'stfp', 'age', 'ids-std |
| 2 | 0.907 | 0.8242 | 0.8621 | 'img_3', 'itp-med', 'dsp-med', 'ncorners', 'age', 'img_1', 'stfp' |
| 3 | 0.904 | 0.8249 | 0.8497 | ['img_3', 'itp-med', 'dsp-med', 'ncorners', 'age', 'img_1', 'stfp', 'ids-std'] |

TABLE 9-continued

The result of each cross validation of Naïve Bayes algorithm

| Times | AUC | Sensitivity | Specificity | Feature Selected |
|---|---|---|---|---|
| 4 | 0.906 | 0.8471 | 0.8286 | ['img_3', 'itp-med', 'dsp-med', 'ncorners', 'age', 'img_1', 'stfp'] |
| 5 | 0.907 | 0.7631 | 0.9061 | ['img_3', 'itp-med', 'dsp-med', 'ncorners', 'age', 'stfp', 'img_1'] |
| 6 | 0.91 | 0.8275 | 0.8571 | ['img_3', 'itp-med', 'dsp-med', 'ncorners', 'img_1', 'stfp', 'age', 'ids-std', 'education'] |
| 7 | 0.912 | 0.816 | 0.8778 | ['img_3', 'itp-med', 'dsp-med', 'ncorners', 'img_1', 'stfp', 'age', 'education'] |
| 8 | 0.912 | 0.8366 | 0.8844 | ['img_3', 'itp-med', 'dsp-med', 'ncorners', 'age', 'img_1', 'stfp', 'education'] |
| 9 | 0.905 | 0.8078 | 0.8686 | ['img_3', 'itp-med', 'dsp-med', 'ncorners', 'img_1', 'stfp', 'age', 'education'] |
| 10 | 0.904 | 0.7804 | 0.8857 | ['img_3', 'itp-med', 'dsp-med', 'ncorners', 'age', 'img_1', 'stfp'] |
| 11 | 0.909 | 0.8217 | 0.8663 | ['img_3', 'itp-med', 'dsp-med', 'ncorners', 'img_1', 'stfp', 'age', 'ids-std'] |
| 12 | 0.878 | 0.75 | 0.9 | ['img_3', 'itp-med', 'dsp-med', 'ncorners', 'age', 'stfp', 'img_1', 'ids-std', 'education'] |
| 13 | 0.911 | 0.8008 | 0.8851 | ['img_3', 'itp-med', 'dsp-med', 'ncorners', 'age', 'img_1', 'stfp', 'education'] |
| 14 | 0.911 | 0.8458 | 0.8475 | ['img_3', 'itp-med', 'dsp-med', 'ncorners', 'age', 'img_1', 'stfp', 'education', 'nclosures'] |
| 15 | 0.908 | 0.7937 | 0.8989 | 'img_3', 'itp-med', 'dsp-med', 'ncorners', 'img_1', 'stfp', 'age', 'education'] |
| 16 | 0.907 | 0.7961 | 0.8971 | ['img_3', 'itp-med', 'dsp-med', 'ncorners', 'img_1', 'stfp', 'age'] |
| 17 | 0.901 | 0.8088 | 0.8715 | ['img_3', 'itp-med', 'dsp-med', 'ncorners', 'img_1', 'age', 'stfp', 'education'] |
| 18 | 0.908 | 0.8196 | 0.8743 | ['img_3', 'itp-med', 'dsp-med', 'ncorners', 'img_1', 'age', 'stfp', 'gender'] |
| 19 | 0.904 | 0.8127 | 0.8659 | ['img_3', 'itp-med', 'dsp-med', 'ncorners', 'age', 'stfp', 'img_1', 'ids-std'] |
| 20 | 0.907 | 0.8110 | 0.875 | ['img_3', 'itp-med', 'dsp-med', 'ncorners', 'education', 'age', 'img_1', 'stfp'] |
| Average | 0.902 | 0.833 | 0.859 | |

Compared to the conventional clinical screening tests for cognitive dysfunctions such as dementia, the drawing process of the subject invention can be captured in real time and as precise as in pixel level by an inexpensive gadget such as a smartphone or a digital tablet. The pixel level drawing data enable further big data analysis and deployment of a high performance prediction model for cognitive dysfunctions screening.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

[1] J. S. Lin et al., "Screening for cognitive impairment in older adults: a systematic review for the US Preventive Services Task Force", Annals of Internal Medicine, 159(9), 2013, pp. 601-612.

[2] B. L. Plassman et al., "Prevalence of dementia in the United States: the aging, demographics, and memory study", Neuroepidemiology, 29(1-2), 2007, pp. 125-132.

[3] V. G. Valcour et al., "The detection of dementia in the primary care setting", Archives of Internal Medicine, 160 (19), 2000, pp. 2964-2968.

[4] J. Chodosh et al., "Physician recognition of cognitive impairment: evaluating the need for improvement", Journal of the American Geriatrics Society, 52(7), 2004, pp. 1051-1059.

[5] S. lliffe, J. Manthorpe, and A. Eden, "Sooner or later? Issues in the early diagnosis of dementia in general practice: a qualitative study", Family Practice, 20(4), 2003, pp. 376-381.

[6] V. G. Valcour et al., "The Detection of dementia in the primary care setting", Archives of Internal Medicine, 160 (19), 2000, pp. 2964-2968.

[7] A. J. Mitchell, "The clinical significance of subjective memory complaints in the diagnosis of mild cognitive impairment and dementia", International Journal of Geriatric Psychiatry, 23(11), 2008, pp. 1191-1202.

[8] A. J. Mitchell, "Risk of dementia and mild cognitive impairment in older people with subjective memory complaints: meta-analysis", Acta Psychiatrica Scandinavica, 130 (6), 2014, pp. 1191-1202.

[9] J. W. Ashford, "Should older adults be screened for dementia?", Alzheimer's & Dementia, 2(2), 2006, pp. 76-85.

[10] W. Souillard-Mandar et al., "Learning classification models of cognitive conditions from subtle behaviors in the digital clock drawing test", Machine Learning, 102(3), 2016, pp. 393-441.

[11] J. M. Oxbury, D. C. Campbell, and S. M. Oxbury, "Unilateral spatial neglect and impairments of spatial analysis and visual perception", Brain, 97(1), 1974, pp. 551-564.

[12] B. H. Lee et al., "Mechanism of the closing-I phenomenon in a figure copying task in Alzheimer's disease patients", Neurocase, 10(5), 2004, pp. 393-397.

[13] S. Dansilio, and A. Charamelo, "Constructional functions and figure copying in illiterates or low-schooled Hispanics", Archives of Clinical Neuropsychology, 20(8), 2005, pp. 1105-1112.

[14] K. Watanabe et al., "The Rey-Osterrieth Complex Figure as a measure of executive function in childhood", Brain and Development, 27(8), 2005, pp. 564-569.

[15] M. S. Shin et al., "Clinical and empirical applications of the Rey-Osterrieth complex figure test", Nature Protocols, 1(2), 2006, pp. 892-899.

[16] J. Tchalenko, and R. C. Miall, "Eye-hand strategies in copying complex lines", Cortex, 45(3), 2009, pp. 368-376.

[17] S. Maechima et al., "Usefulness of a Cube-Copying Test in Outpatients with Dementia", Brain Injury, 18(9), 2004, pp. 889-898.

[18] P. Buchhave et al., "Cube Copying Test in Combination with rCBF or CSF Aβ42Predicts Development of

[19] J. Bourke et al., "A comparison of clock and pentagon drawing in Alzheimer's disease". International Journal of Geriatric Psychiatry, 10(8), 1995, pp. 703-705.

[20] T. A. Ala et al., "Pentagon copying is more impaired in dementia with Lewy bodies than in Alzheimer's disease", Journal of Neurology, Neurosurgery, and Psychiatry, 70(4), 2001, pp. 483-488.

[21] F. Cormack et al. "Pentagon drawing and neuropsychological performance in Dementia with Lewy Bodies, Alzheimer's disease, Parkinson's disease and Parkinson's disease with dementia", International journal of geriatric psychiatry, 19(4), 2004, pp. 371-377.

[22] P. Caffarra et al., "The qualitative scoring MMSE pentagon test (QSPT): a new method for differentiating dementia with Lewy body from Alzheimer's disease" Behavioural Neurology, 27(2), 2013, pp. 213-220.

[23] M. Mitolo et al., "The new Qualitative Scoring MMSE Pentagon Test (QSPT) as a valid screening tool between autopsy-confirmed dementia with Lewy bodies and Alzheimer's disease", Journal of Alzheimer's Disease, 39(4), 2014, pp. 823-832.

[24] A. Cagnin et al., "High specificity of MMSE pentagon scoring for diagnosis of prodromal dementia with Lewy bodies", Parkinsonism & related disorders, 21(3), 2015, pp. 303-305.

[25] Alzheimer's Society (2016). Risk factors for dementia. Alzheimer's Society, pp.1-17.

We claim:

1. A method for screening, diagnosing, or predicting presence, progression, or treatment effects of cognitive dysfunction based on analysis of drawing behavior changes, comprising:
 a) obtaining drawing data of at least one image created by a test subject on a digital device and obtaining personal data of the test subject;
 b) reconstructing the at least one image based on the drawing data obtained;
 c) converting the drawing data to drawing features comprising a plurality of motion features and a plurality of geometric features; and
 d) determining a probability that the test subject has a cognitive dysfunction based on the drawing features and the personal data by a pre-trained Naïve Bayes method
 wherein the reconstructing the image created comprises:
 a) filtering an entire drawing trajectory of the at least one image to reassemble separated drawing segments;
 b) re-drawing the figure pixel by pixel based on drawing segments obtained in the filtering and stored for processing; and
 c) resizing the image to a predetermined size and converting the image into greyscale.

2. The method of claim 1, wherein the obtaining the drawing data comprises obtaining the drawing data from both the at least one image created and the process of creating the at least one image.

3. The method of claim 1, wherein the at least one image is recorded in real time with a pixel level precision by the digital device.

4. A method for screening, diagnosing, or predicting presence, progression, or treatment effects of cognitive dysfunction based on analysis of drawing behavior changes, comprising:
 a) obtaining drawing data of at least one image created by a test subject on a digital device and obtaining personal data of the test subject;
 b) reconstructing the at least one image based on the drawing data obtained;
 c) converting the drawing data to drawing features comprising a plurality of motion features and a plurality of geometric features; and
 d) determining a probability that the test subject has a cognitive dysfunction based on the drawing features and the personal data by a pre-trained Naïve Bayes method,
 wherein the drawing data comprises continuous drawing trajectory including coordinates, time spent, and whether a point is an end of a touch on the digital device for each pixel drawn by the test subject.

5. The method of claim 1, wherein the at least one image comprises at least two interlocking pentagons.

6. The method of claim 1, wherein the personal data comprise information of age, gender, and education level of the test subject.

7. The method of claim 1, wherein the converting the drawing data to drawing features comprises removing statistical outliers of the drawing data and then performing predefined mathematical formulas for obtaining the plurality of motion features and the geometric features, and performing Principal Component Analysis (PCA) statistical procedures on the drawing data for obtaining extended geometric features.

8. The method of claim 1, wherein the plurality of motion features comprises at least one of summary statistics including mean and/or maximum and/or minimum and/or standard deviation and/or median of drawing time at a pixel or stroke or shape level, drawing distance at a pixel or stroke or shape level, stopping time at a shape level, or drawing speed at a pixel or stroke level.

9. The method of claim 1, wherein the plurality of geometric features comprises at least one of a number of corners of the at least one image or a number of closed shapes of the at least one image.

10. A method for screening, diagnosing, or predicting presence, progression, or treatment effects of cognitive dysfunction based on analysis of drawing behavior changes, comprising:
 a) obtaining drawing data of at least one image created by a test subject on a digital device and obtaining personal data of the test subject;
 b) reconstructing the at least one image based on the drawing data obtained;
 c) converting the drawing data to drawing features comprising a plurality of motion features and a plurality of geometric features; and
 d) determining a probability that the test subject has a cognitive dysfunction based on the drawing features and the personal data by a pre-trained Naïve Bayes method,
 wherein the plurality of geometric features comprises at least one of a number of corners of the at least one image or a number of closed shapes of the at least one image, and wherein the converting the drawing data to the number of closed shapes of the plurality of geometric features comprises:
a) filtering the drawing data based on instantaneous drawing speeds;
b) converting drawing data into a set of connected stokes by connecting any two pixels that are spaced apart from each other by a distance smaller than a threshold value;
c) filtering the set of connected stokes into a polygon, if a starting point and an ending point of each connected stroke are spaced apart from each other by a distance smaller than the threshold value; and
d) determining the number of closed shapes to be a number of groups in the filtering the set of connected stokes into the polygon that has at least a predetermined number of connected strokes.

11. A method for screening, diagnosing, or predicting presence, progression, or treatment effects of cognitive dysfunction based on analysis of drawing behavior changes, comprising:
a) obtaining drawing data of at least one image created by a test subject on a digital device and obtaining personal data of the test subject;
b) reconstructing the at least one image based on the drawing data obtained;
c) converting the drawing data to drawing features comprising a plurality of motion features and a plurality of geometric features; and
d) determining a probability that the test subject has a cognitive dysfunction based on the drawing features and the personal data by a pre-trained Naïve Bayes method,
wherein the plurality of geometric features comprises at least one of a number of corners of the at least one image or a number of closed shapes of the at least one image, and
wherein the converting the drawing data to the number of corners of the plurality of geometric features comprises:
a) filtering the drawing data based on instantaneous drawing speeds;
b) converting drawing data into a set of connected stokes by connecting any two pixels that are spaced apart from each other by a distance smaller than a first threshold value;
c) calculating a number of mid-points, if the following condition is satisfied: a sum of a distance between a starting point and a mid-point of a connected stroke and an ending point and the mid-point of the connected stroke is larger than a distance between the starting point and the ending point of the connected stroke; and
d) performing clustering if mid-points are spaced apart from each other by a distance smaller than a second threshold value.

12. The method of claim 1, wherein the cognitive dysfunction includes dementia.

13. A method for developing a prediction method for screening, diagnosing, or predicting presence, progression, or treatment effects of a cognitive dysfunction based on an analysis of drawing behavior changes, comprising:
a) collecting personal data and drawing data of at least one image created by clinically diagnosed and/or screened subjects with the cognitive dysfunction and from subjects without the cognitive dysfunction;
b) converting the drawing data to drawing features, comprising a plurality of motion features and a plurality of geometric features;

c) reconstructing the at least one image based on the drawing data collected;
d) performing Principal Component Analysis statistical procedures on the drawing data to obtain a plurality of extended geometric features and storing the obtained plurality of eigenvectors of the extended geometric features;
e) selecting key motion features from the plurality of motion features by removing summary statistics with a high correlation, performing a group removal on each group of motion features, and removing motion features that are of similar clinical meaning; and
f) developing a pre-trained method based on a Naïve Bayes method with a greedy variable selection for performing on the motion features, the geometric features, the extended geometric features, and the key motion features.

14. The method of claim 13, wherein the converting the drawing data to drawing features comprises performing predefined mathematical formulas for obtaining the plurality of motion features and the geometric features.

15. The method of claim 13, wherein the motion features comprise: at least one of summary statistics including mean and/or maximum and/or minimum and/or standard deviation and/or median of drawing time at a pixel or stroke or shape level, drawing distance at a pixel or stroke or shape level, stopping time at a shape level, or drawing speed at a pixel or stroke level.

16. The method of claim 13, wherein the plurality of geometric features comprises at least one of a number of corners of the at least one image, a number of closed shapes of the at least one image, and a minimum distance between every two corners of the closed shapes.

17. The method of claim 13, wherein the Naïve Bayes method with a greedy variable selection comprises:
a) starting with no drawing features in the method;
b) at each step, adding one drawing feature to the method, in which the drawing feature generates a largest performance improvement to a cross-validated Area Under Curve;
c) stopping adding features when there is no improvement to the method; and
d) fitting the selected drawing features with a pre-defined distribution and saving results for prediction.

18. A non-transitory computer-readable medium comprising program instructions stored thereon that, when executed, cause a processor to perform a method for screening, diagnosing, or predicting presence, progression, or treatment effects of cognitive dysfunction based on an analysis of drawing behavior changes, comprising:
a) obtaining drawing data of at least one image created by a test subject on a digital device and obtaining personal data of the test subject;
b) reconstructing the at least one image based on the drawing data obtained;
c) converting the drawing data to drawing features comprising a plurality of motion features and a plurality of geometric features; and
d) determining a probability that the test subject has a cognitive dysfunction based on the drawing features and the personal data by a pre-trained Naïve Bayes method,
wherein the reconstructing the image created comprises:
a) filtering an entire drawing trajectory of the at least one image to reassemble separated drawing segments;

b) re-drawing the figure pixel by pixel based on drawing segments obtained in the filtering and stored for processing; and c) resizing the image to a predetermined size and converting the image into greyscale.

19. A non-transitory computer-readable medium comprising program instructions stored thereon that, when executed, cause a processor to perform a method for developing a prediction method for screening, diagnosing, or predicting presence, progression, or treatment effects of a cognitive dysfunction based on an analysis of drawing behavior changes, comprising:

a) collecting personal data and drawing data of at least one image created by clinically diagnosed and/or screened subjects with the cognitive dysfunction and from subjects without the cognitive dysfunction;

b) converting the drawing data to drawing features, comprising a plurality of motion features and a plurality of geometric features;

c) reconstructing the at least one image based on the drawing data collected;

d) performing Principal Component Analysis statistical procedures on the drawing data to obtain a plurality of extended geometric features and storing the obtained plurality of eigenvectors of the extended geometric features;

e) selecting key motion features from the plurality of motion features by removing summary statistics with high correlation, performing a group removal on each group of motion features, and removing motion features that are of similar clinical meaning; and f) developing a pre-trained method based on a Naïve Bayes method with a greedy variable selection for performing on the motion features, the geometric features, the extended geometric features, and the key motion features.

20. The method of claim 1, wherein the drawing data comprises continuous drawing trajectory including coordinates, time spent, and whether a point is an end of a touch on the digital device for each pixel drawn by the test subject.

* * * * *